US012661186B2

(12) United States Patent　　　　　　(10) Patent No.:　US 12,661,186 B2
Cameron et al.　　　　　　　　　　　　(45) Date of Patent:　　Jun. 23, 2026

(54) INSTRUMENTS FOR NAVIGATED ORTHOPEDIC SURGERIES

(71) Applicant: GLOBUS MEDICAL, INC., Audubon, PA (US)

(72) Inventors: Hayden Cameron, Philadelphia, PA (US); Olivier Chappuis, Lutry (CH); Szymon Kostrzewski, Lausanne (CH); Benoit Brot, Lausanne (CH); Peter Eckert, Renens (CH); Stephen Cicchini, North Wales, PA (US); Neil R. Crawford, Chandler, AZ (US); Jason Zappacosta, Philadelphia, PA (US); Drew Mike, Phoenixville, PA (US); David Stumpo, Collegeville, PA (US); Timothy Blackwell, Ft. Pierce, FL (US)

(73) Assignee: Globus Medical, Inc., Audubon, PA (US)

( * ) Notice: Subject to any disclaimer, the term of this patent is extended or adjusted under 35 U.S.C. 154(b) by 37 days.

(21) Appl. No.: 18/418,421

(22) Filed: Jan. 22, 2024

(65) Prior Publication Data

US 2024/0225749 A1　　Jul. 11, 2024

Related U.S. Application Data

(63) Continuation of application No. 16/925,884, filed on Jul. 10, 2020, now Pat. No. 11,877,807.

(51) Int. Cl.
*A61B 34/20*　　　(2016.01)
*A61B 34/10*　　　(2016.01)

*A61B 34/37*　　　(2016.01)
*A61B 90/00*　　　(2016.01)

(52) U.S. Cl.
CPC .............. *A61B 34/20* (2016.02); *A61B 34/10* (2016.02); *A61B 34/37* (2016.02); *A61B 90/39* (2016.02); *A61B 2034/105* (2016.02); *A61B 2034/107* (2016.02); *A61B 2034/2055* (2016.02); *A61B 2034/2068* (2016.02); *A61B 2090/3916* (2016.02)

(58) Field of Classification Search
None
See application file for complete search history.

(56) References Cited

U.S. PATENT DOCUMENTS

| 4,150,293 | A | | 4/1979 | Franke | |
|---|---|---|---|---|---|
| 4,501,266 | A | * | 2/1985 | McDaniel | ............ A61B 17/025 |
| | | | | | 606/88 |
| 5,246,010 | A | | 9/1993 | Gazzara et al. | |

(Continued)

FOREIGN PATENT DOCUMENTS

JP　　　2006500182 A　　　1/2006

OTHER PUBLICATIONS

US 8,231,638 B2, 07/2012, Swarup et al. (withdrawn)

*Primary Examiner* — Yi-Shan Yang

(57) ABSTRACT

Devices, systems, and methods for computer-assisted navigation and/or robot-assisted surgery. Navigable instrumentation, which are capable of being navigated by a surgeon using the surgical robot system, allow for the navigated movement of instruments or other surgical devices. The instruments may be suitable for procedures involving navigated and/or robotic total knee arthroplasty, for example.

16 Claims, 23 Drawing Sheets

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |

(56) References Cited

U.S. PATENT DOCUMENTS

| | | | |
|---|---|---|---|
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |

(56)  References Cited

U.S. PATENT DOCUMENTS

| | | |
|---|---|---|
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Tott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 12/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0016009 A1 | 1/2007 | Lakin et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |

(56) References Cited

U.S. PATENT DOCUMENTS

| | | |
|---|---|---|
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0244488 A1 | 10/2007 | Metzger et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0200794 A1 | 8/2008 | Teichman et al. |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |

(56)                References Cited

U.S. PATENT DOCUMENTS

| | | |
|---|---|---|
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2017/0360512 A1 | 12/2017 | Couture et al. |
| 2019/0008501 A1* | 1/2019 | Plaskos ............... A61B 17/025 |
| 2019/0228859 A1 | 7/2019 | De La Barrera |

* cited by examiner

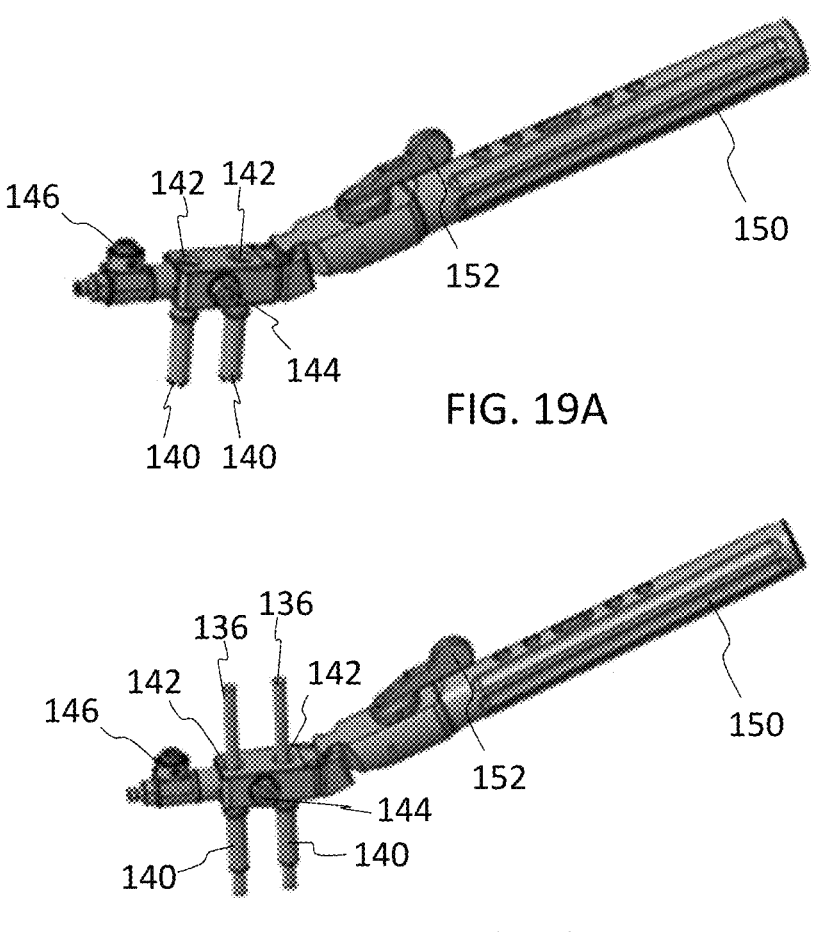
FIG. 19A
FIG. 19B
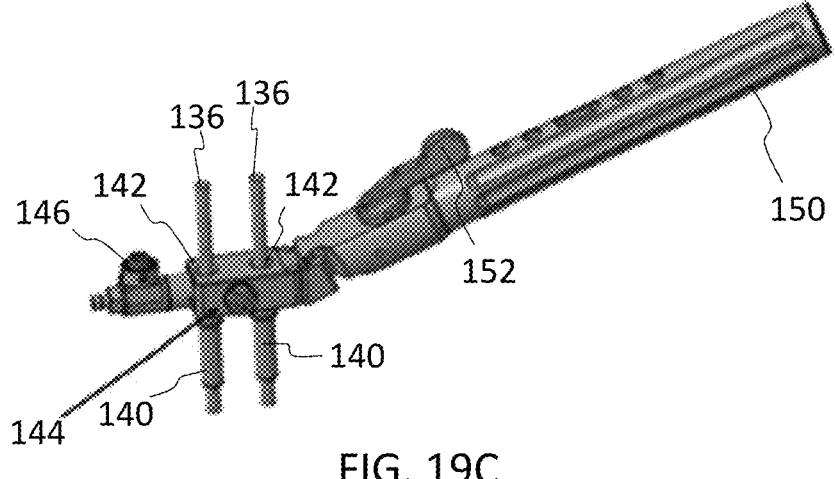
FIG. 19C

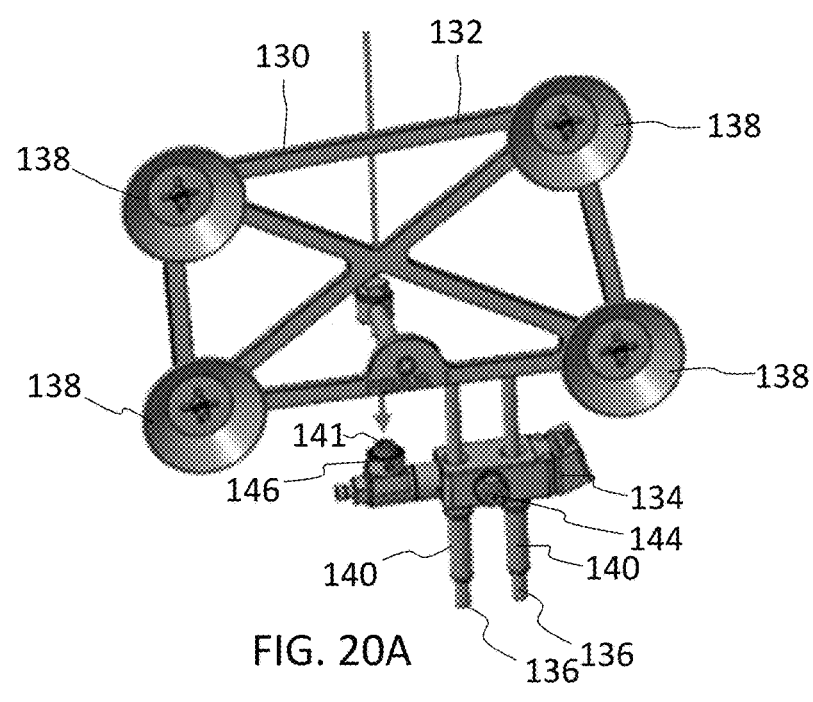
FIG. 20A
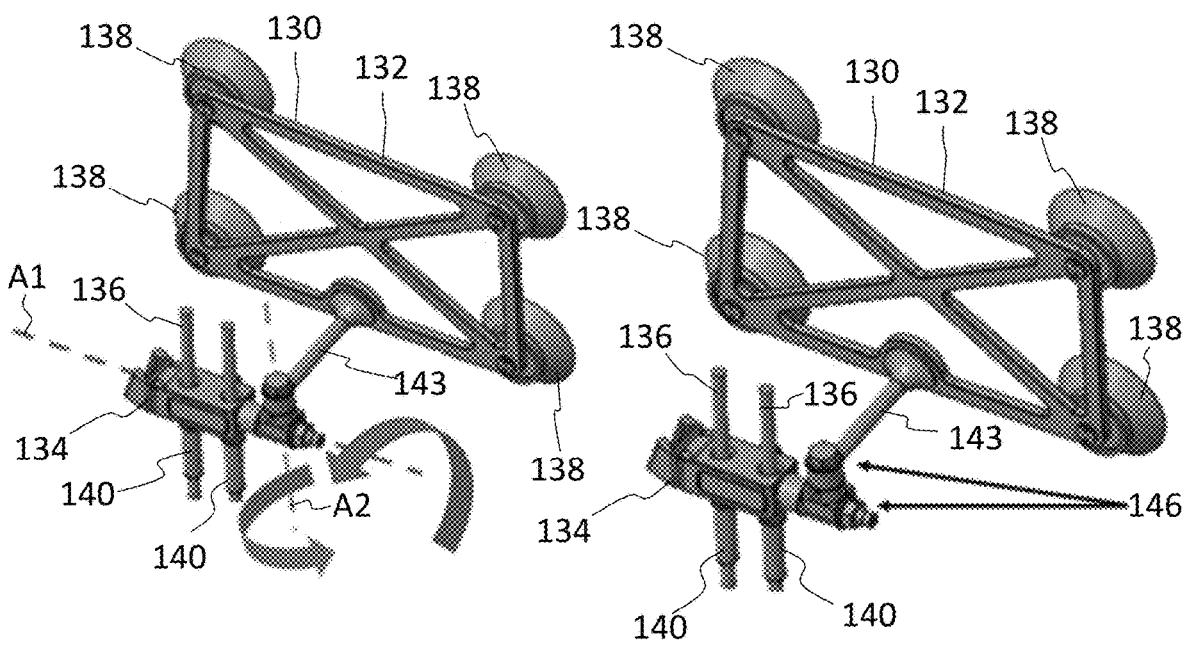
FIG. 20B                    FIG. 20C

INSTRUMENTS FOR NAVIGATED ORTHOPEDIC SURGERIES

CROSS-REFERENCE TO RELATED APPLICATIONS

The present application is a continuation of U.S. patent application Ser. No. 16/925,884, filed on Jul. 10, 2020, which is incorporated herein it its entirety for all purposes.

FIELD OF THE INVENTION

The present disclosure relates to medical devices and systems, and more particularly, to navigated surgical instruments for use during surgical procedures.

BACKGROUND OF THE INVENTION

There are a number of surgical interventions requiring osteotomy, e.g., cutting an anatomical structure, such as a bone, along a target plane. A total knee arthroplasty (TKA) may involve cutting both the femoral epiphysis and tibial epiphysis to remove the damaged bone and cartilage and allow for installation of a knee prosthesis.

Currently in TKA surgeries, the patient satisfaction rate may only be about 80%. This is low in comparison to some other types of orthopedic surgeries, such as for hip arthroplasty where patient satisfaction is typically about 95%. These satisfaction rates have remained principally unchanged over several decades despite innovations in new implant designs, custom cutting template solutions, customized implants, and the like. This suggests that there may be problems with TKA and other orthopedic surgeries that have not been addressed by previous medical procedures and related innovations.

Computer-assisted surgery (CAS) including navigation and/or robotic surgical systems may utilize position recognition systems, which determine the position of and track a particular object in 3-dimensions (3D). In navigation and/or robot-assisted surgeries, certain objects, such as surgical instruments, need to be tracked with a high degree of precision as the instrument is being positioned and moved by the surgeon and/or by the robot, for example. There is also a need to provide improved instrumentation for use with navigated and/or robot-assisted surgeries.

SUMMARY OF THE INVENTION

To meet this and other needs, and in view of its purposes, the present application provides devices, systems, instruments, and methods for performing orthopedic operations, such as a total knee arthroplasty (TKA). A surgical robotic system and/or navigation system may be provided which navigates one or more instruments and/or assists a user with one or more surgical procedures. Navigable instrumentation, which includes instruments capable of being navigated, and navigation software allow for navigation of the instruments or other surgical devices. The system allows for locating anatomical structures in open or minimally invasive (MIS) procedures and navigation of surgical instruments and other devices throughout the procedure.

According to one embodiment, a system for computer-assisted navigation during surgery includes a robotic navigation system, first and second dynamic reference bases, and a navigable stylus. The robotic navigation system may include a computer, a display, and a camera configured to detect one or more tracking markers. The first dynamic reference base may include a first reference array with a first plurality of tracking markers, and the first dynamic reference base may be configured to attach to and track a first bone. The second dynamic reference base may include a second reference array with a second plurality of tracking markers, and the second dynamic reference base may be configured to attach to and track a second bone. The navigable stylus may include a third reference array with a third plurality of tracking markers and a universal quick-connect attachment tip configured to quickly attach the stylus to one or more instruments and return a position to the robotic navigation system. When used during a total knee arthroplasty, the first bone may be a femur and the second bone may be a tibia or vice versa. The femur and tibia may be positioned in flexion or extension during the procedure.

The instrument may be a posterior tibial wall hook or a plane checker, for example. The posterior tibial wall hook may include a collar and a hook. The collar may include a longitudinal opening configured to receive the universal tip, and the hook may be configured to localize a tibial wall during the total knee arthroplasty. The plane checker may include a collar and a foot. The collar may include a longitudinal opening configured to receive the universal tip, and the foot may include a U-shaped plate with a flat bottom surface configured to be placed on a resection plane to return an angulation and/or cut depth to the robotic navigation system. The instrument may be free to rotate relative to a longitudinal axis of the stylus, thereby allowing quick reorientation of the third reference array, for example, to facilitate line of sight with the camera.

According to another embodiment, a system for computer-assisted navigation during surgery includes a robotic navigation system, first and second dynamic reference bases, and one or more surveillance markers. For example, a first surveillance marker may be configured to attach to a first bone (one of the femur or tibia), and a second surveillance marker may be configured to attach to a second bone (the other femur or tibia). The surveillance marker may include a body including a fastener (e.g., a bone pin) terminating at a distal tip and a single tracking marker on top of the surveillance marker. The surveillance marker may include a verification divot integrated into the body of the surveillance marker. The verification divot may be configured to verify navigational integrity of the system by placing a tip of a separate instrument (e.g., the stylus) into the verification divot of the surveillance marker.

According to another embodiment, a system for computer-assisted navigation during surgery includes a robotic navigation system, first and second dynamic reference bases, and one or more virtual landmarks. For example, a first virtual landmark may be configured to attach to the first bone and a second virtual landmark may be configured to attach to the second bone. The virtual landmark may include a cortical bone screw with a verification divot, for example. The virtual landmark may be configured to verify navigational integrity of the system by placing a tip of a separate instrument (e.g., the stylus) into the verification divot of the virtual landmark.

According to yet another embodiment, a system for computer-assisted navigation during surgery includes a robotic navigation system and one or more dynamic reference bases configured to attach to and track bone. The dynamic reference base may include a single surveillance marker. A distance between the reference array of the dynamic reference base and the surveillance marker is stored by the system. If the dynamic reference base and/or surveillance marker is inadvertently moved, a change in distance and/or movement is identified by the system, thereby alter-ing the user to the disruption.

According to yet another embodiment, a system for computer-assisted navigation during surgery includes a robotic navigation system, first and second dynamic refer-ence bases, and a navigable plane checker. The plane checker may include a body with a reference array including a plurality of tracking markers, a shaft extending from the body, and a foot at a distal end of the shaft. When used during a knee procedure, the plane checker may be placed against the resection to ensure that the angulation and/or location of the resection is correct.

According to yet another embodiment, a system for computer-assisted navigation during surgery includes a robotic navigation system, first and second dynamic refer-ence bases, and a navigable stylus configured for landmark localization and/or point acquisition. When the stylus is on a landmark or point of interest, the stylus may be rotated by a threshold rotation (e.g., at least 30°). The threshold rotation may be captured by the robotic navigation system, thereby capturing the landmark or point of interest by the robotic navigation system. In another embodiment, one tracking marker associated with the reference array of the stylus may be physically movable relative to the other tracking markers. When the stylus is on a landmark or point of interest, the robotic navigation system detects the movement of the one tracking marker relative to the other tracking markers and captures the landmark or point of interest.

According to yet another embodiment, a system for computer-assisted navigation during surgery includes a robotic navigation system, first and second dynamic refer-ence bases, and a tensor including a body with a pair of independent superior distraction paddles, an inferior distrac-tion paddle, a shaft connected to a knob configured to move the superior distraction paddles relative to the inferior dis-traction paddle, and a spring positioned around the shaft between the body and the knob. The tensor may be config-ured to provide a distraction force between the tibia and the femur. For example, rotation of the distraction knob may translate the superior distraction paddles outwardly and away from the inferior distraction paddle, thereby providing a gap between the superior and inferior distraction paddles. The tensor may include a pivotable ligament balance indi-cator positioned on the body of the tensor. The first superior distraction paddle may be connected to a first end of the ligament balance indicator with a first rod, and the second superior distraction paddle may be connected to the opposite end of the ligament balance indicator with a second rod. When distracted, for example, during a knee procedure, the tensor is configured to apply a distraction force $F_{DISTRAC-TION}$ against the inferior distraction paddle, a force $F_{LCL}$ (lateral collateral ligament) against the first superior distrac-tion paddle, and a force $F_{MCL}$ (medial collateral ligament) against the second superior distraction paddle. When the ligaments are in balance where $F_{LCL}=F_{MCL}$, the ligament balance indicator indicates the balance, for example, by showing the indicator in a horizontal position. When the ligaments are not in balance where $F_{LCL}<F_{MCL}$ or $F_{LCL}>F_{MCL}$, then the ligament balance indicator indicates the imbalance, for example, by showing the indicator in a sloped, inclined, or slanted position. The indicator may also indicate the amount or degree of imbalance for each respec-tive force.

According to yet another embodiment, a system for computer-assisted navigation during surgery includes a robotic navigation system and one or more modular dynamic reference bases. The modular dynamic reference base may include a reference array with a plurality of tracking mark-ers, an integrated bridge and pin guide, and one or more fasteners. Each of the plurality of tracking markers may be positioned within a protective shield configured to prevent loss of navigation. The bridge may include a first opening aligned with a first pin guide and a second opening aligned with a second pin guide. First and second fasteners may be receivable through the bridge and pin guides for securing the dynamic reference base to bone. The reference array may include a rectangular frame with a cross brace, and a tracking marker placed at each corner of the rectangular frame within each respective shield. The reference array may be configured to rotate about two axes, for example. The array may be able to rotate about a longitudinal axis of the bridge and/or about an axis perpendicular to the bridge. After adjustment along one or both of the axes, the reference array may be locked into position with one or more locking screws. If desired, an extension arm may be used to increase positioning options for the reference array. The bridge may temporarily attach to a removable handle for installation. The modular components of the dynamic reference base may reduce the number of instruments used throughout the procedure.

According to yet another embodiment, a method of installing the modular dynamic reference base may include one or more of the following in any suitable order: (1) making incision(s) into the patient; (2) attaching a handle to an integrated bridge and pin guide; (3) inserting the bridge in the incision until the bridge contacts cortical bone; (4) driving one or more bone pins through the bridge and pin guide; (5) locking the bridge to the pins, for example, using a locking screw; (6) removing the handle from the bridge; (7) attaching the reference array to the bridge; (8) optionally, attaching an extension between the reference array and the bridge to facilitate more positioning options for the refer-ence array; (9) adjusting the orientation of the reference array, for example, along one or two axes; and (10) locking the final position of the reference array relative to the bridge via one or more locking screws.

Also provided are kits including navigable instruments and components of varying types and sizes, implants, fas-teners or anchors, k-wires, insertion tools, and other com-ponents for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

5

Figures 7A, 7B:
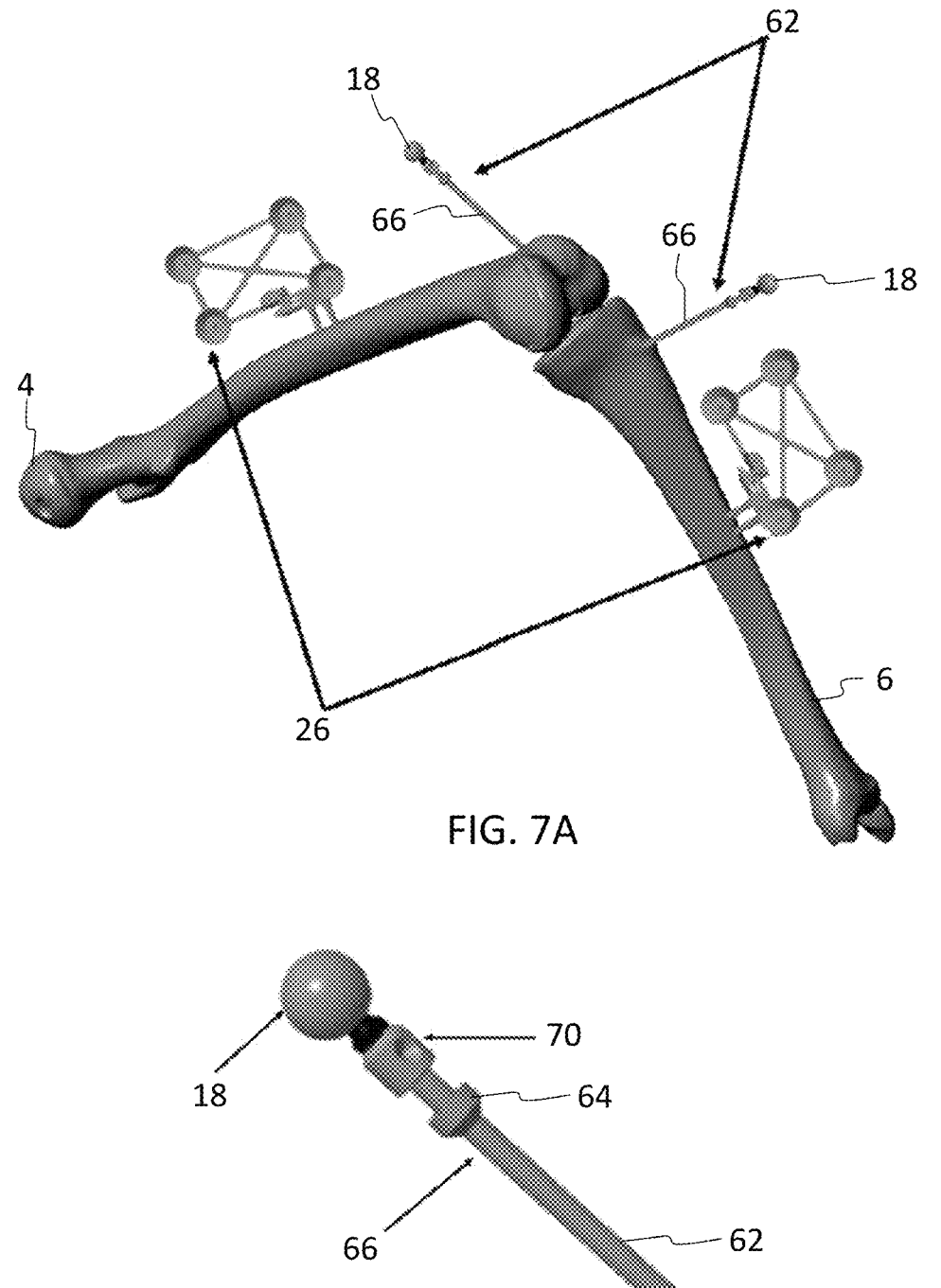
Figure 8:
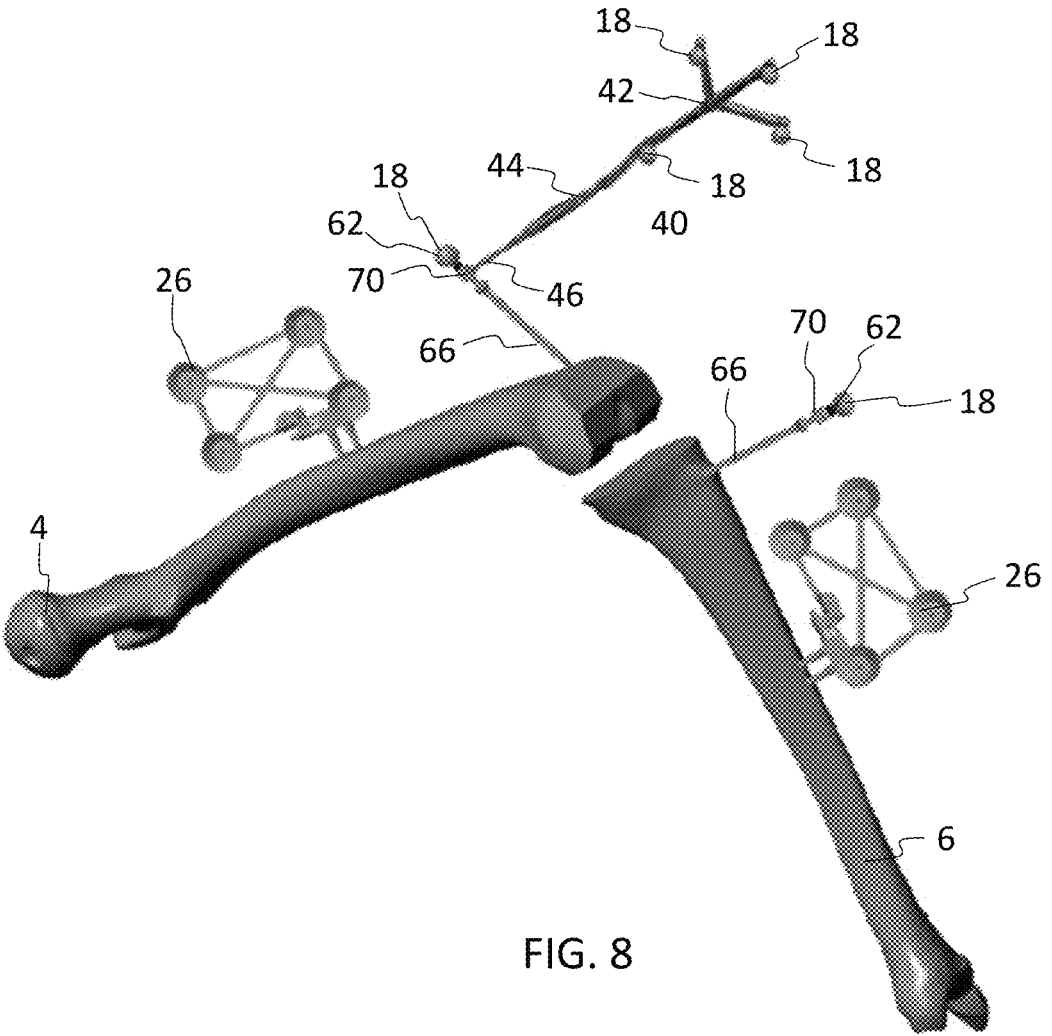
Figure 9A:
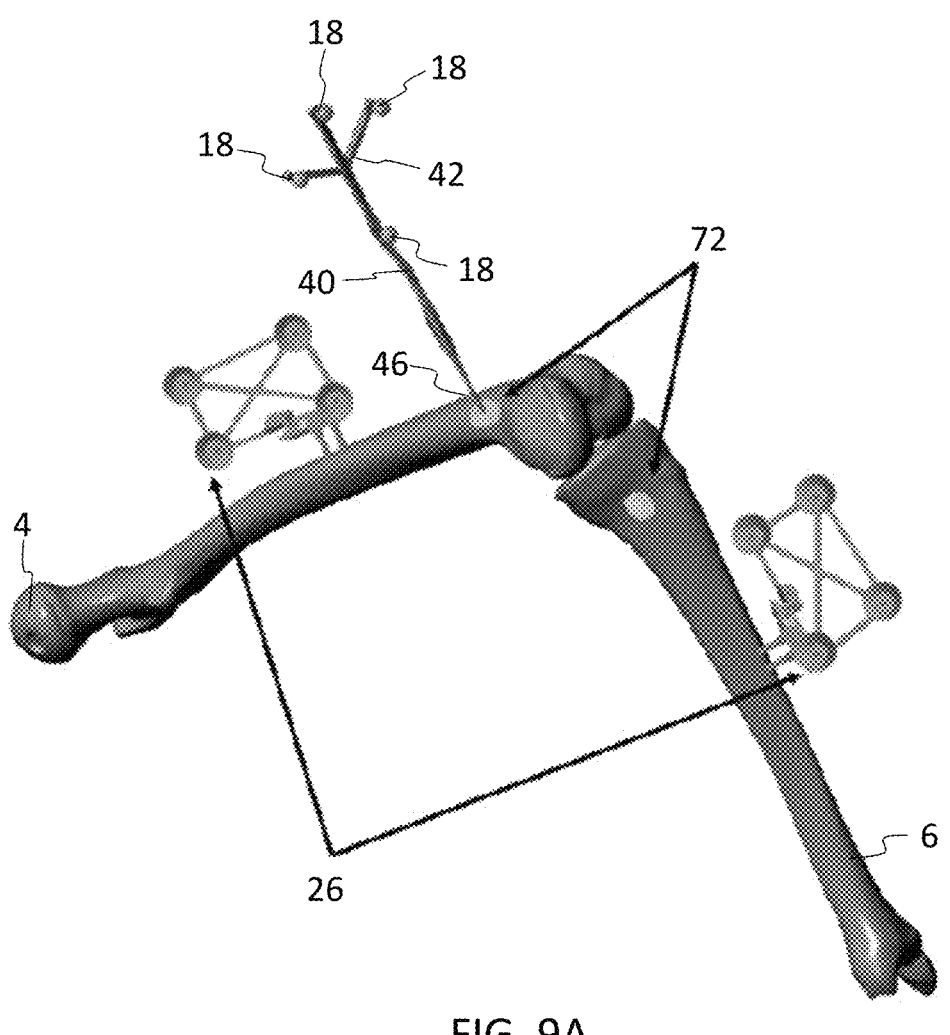
Figure 9B:
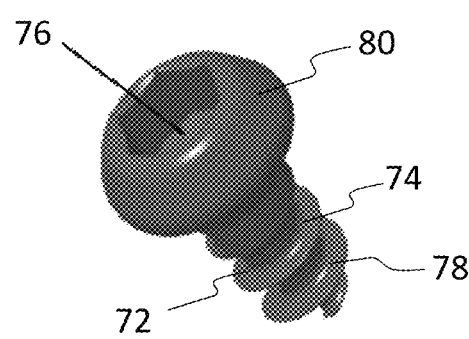
Figure 10:
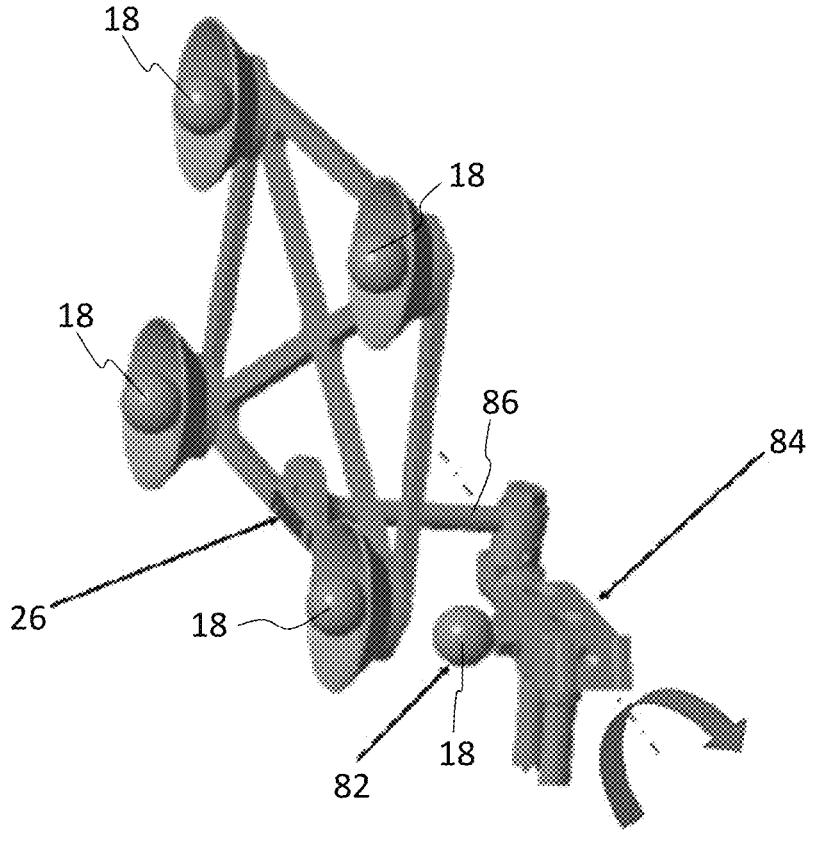
Figure 11A:
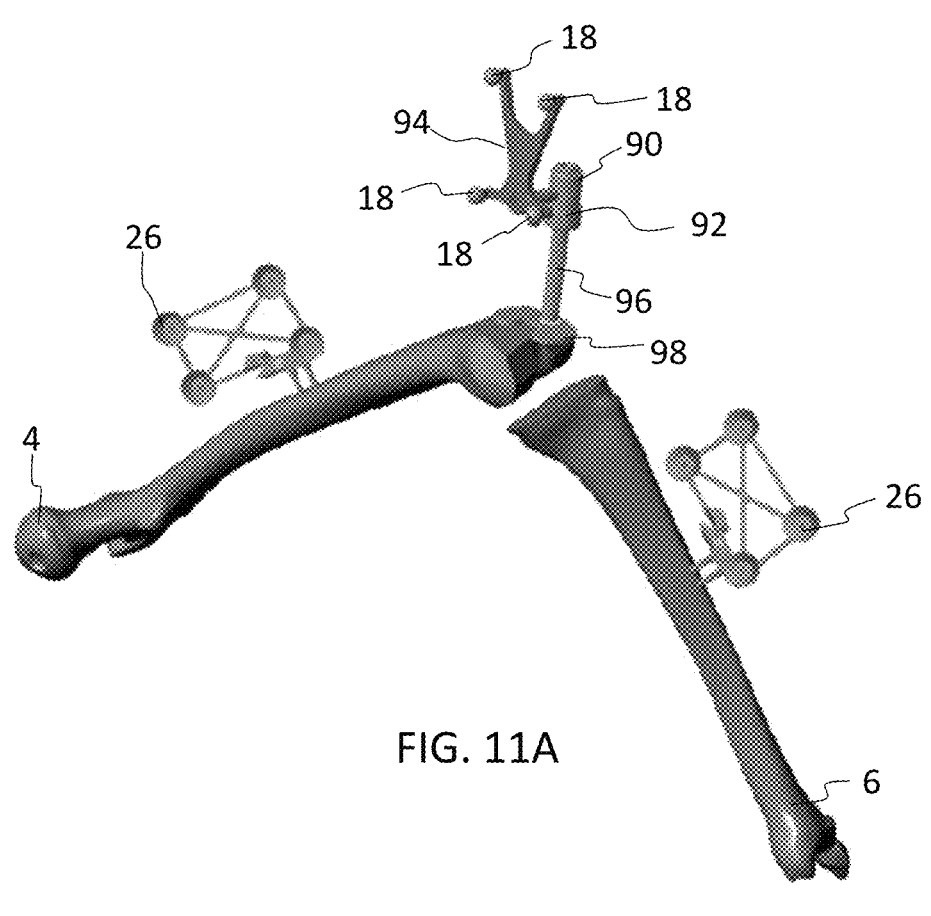
Figure 11B:
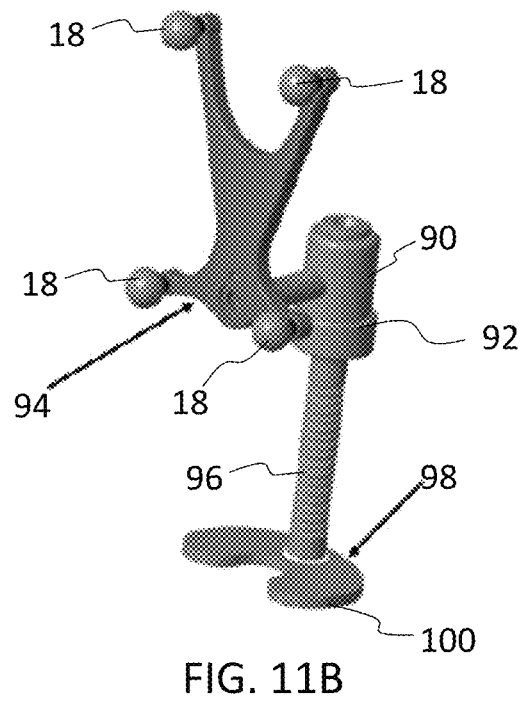
Figures 12A, 12B:
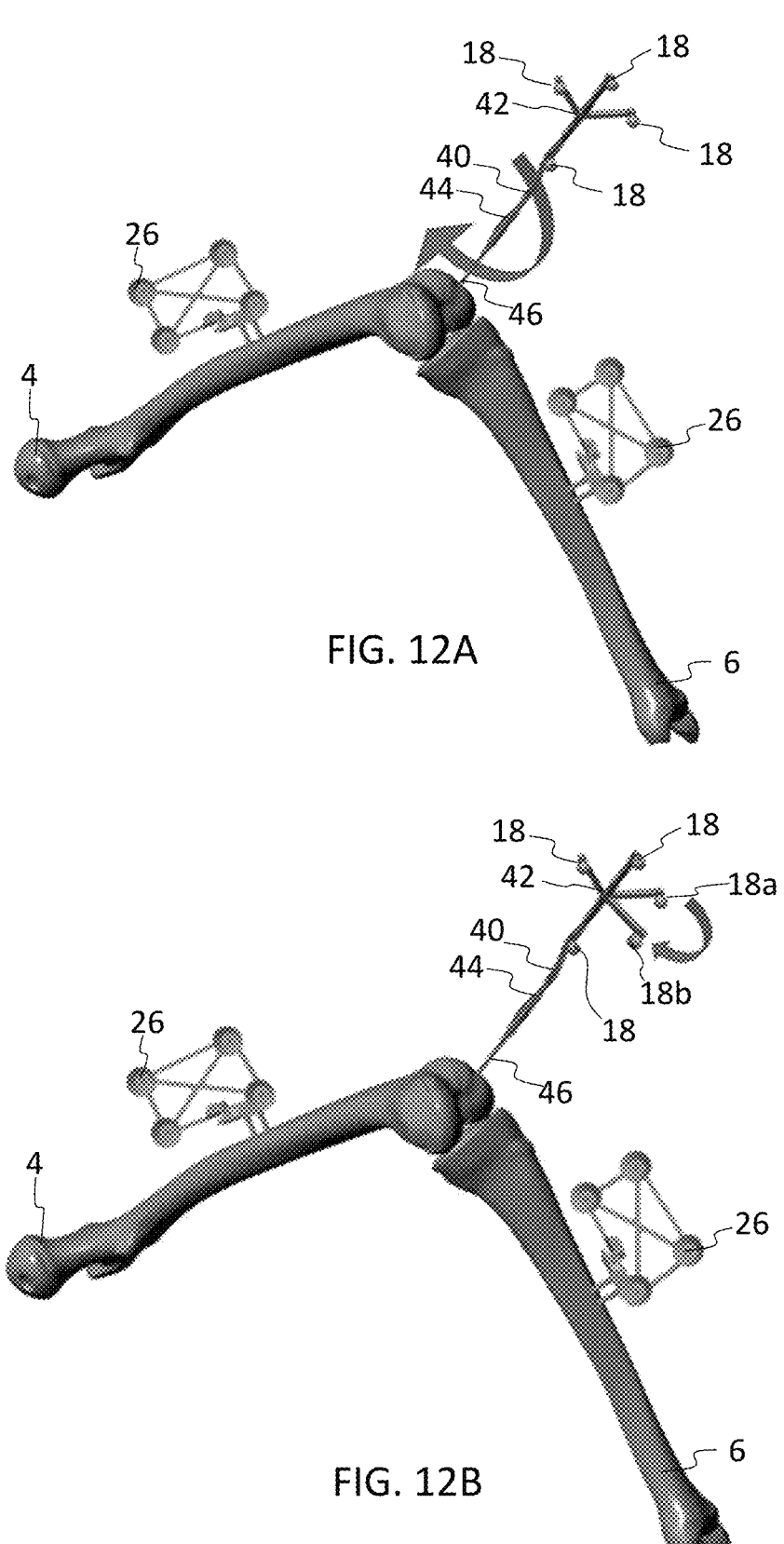
Figures 13, 14:
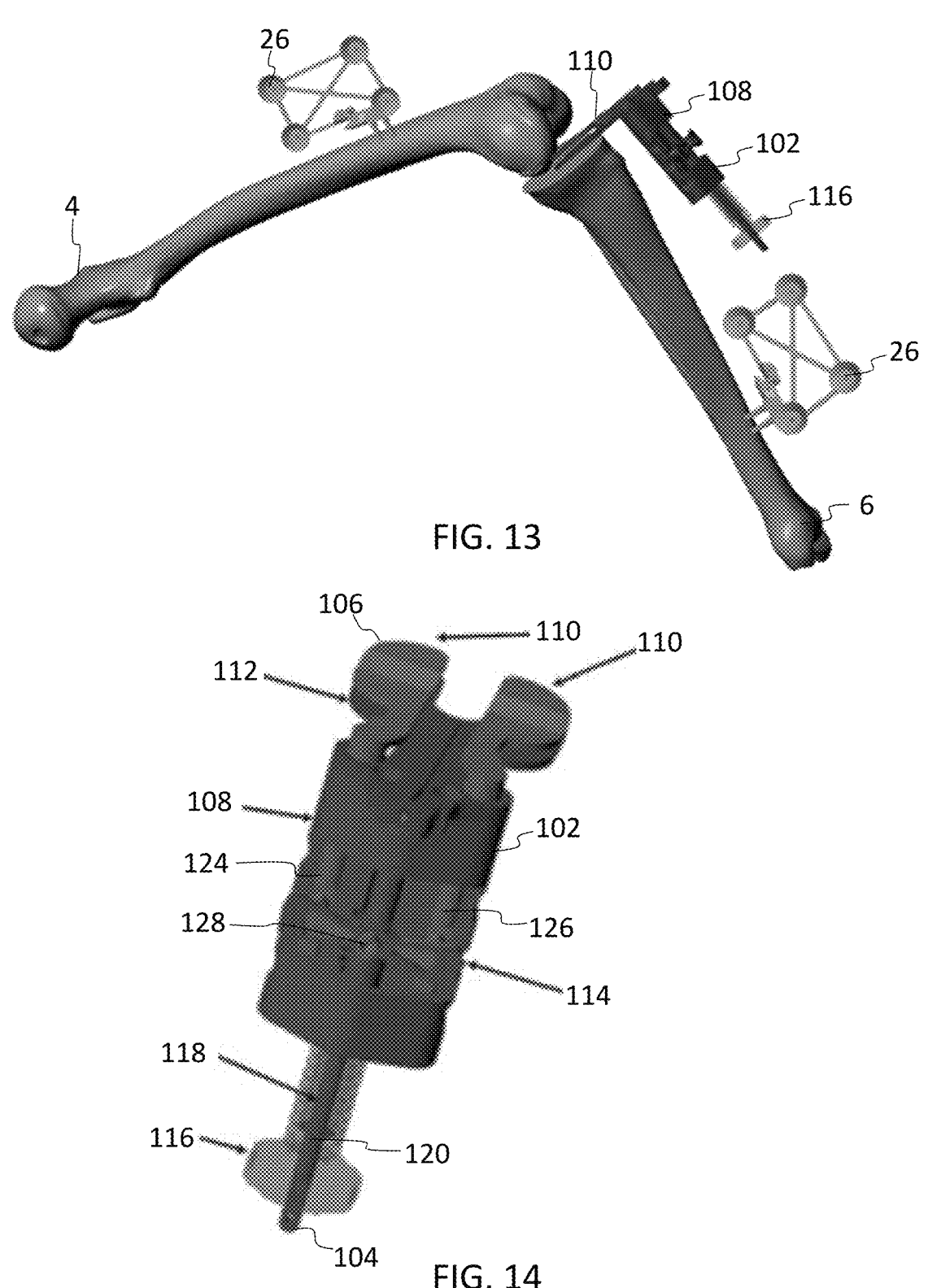
Figure 15:
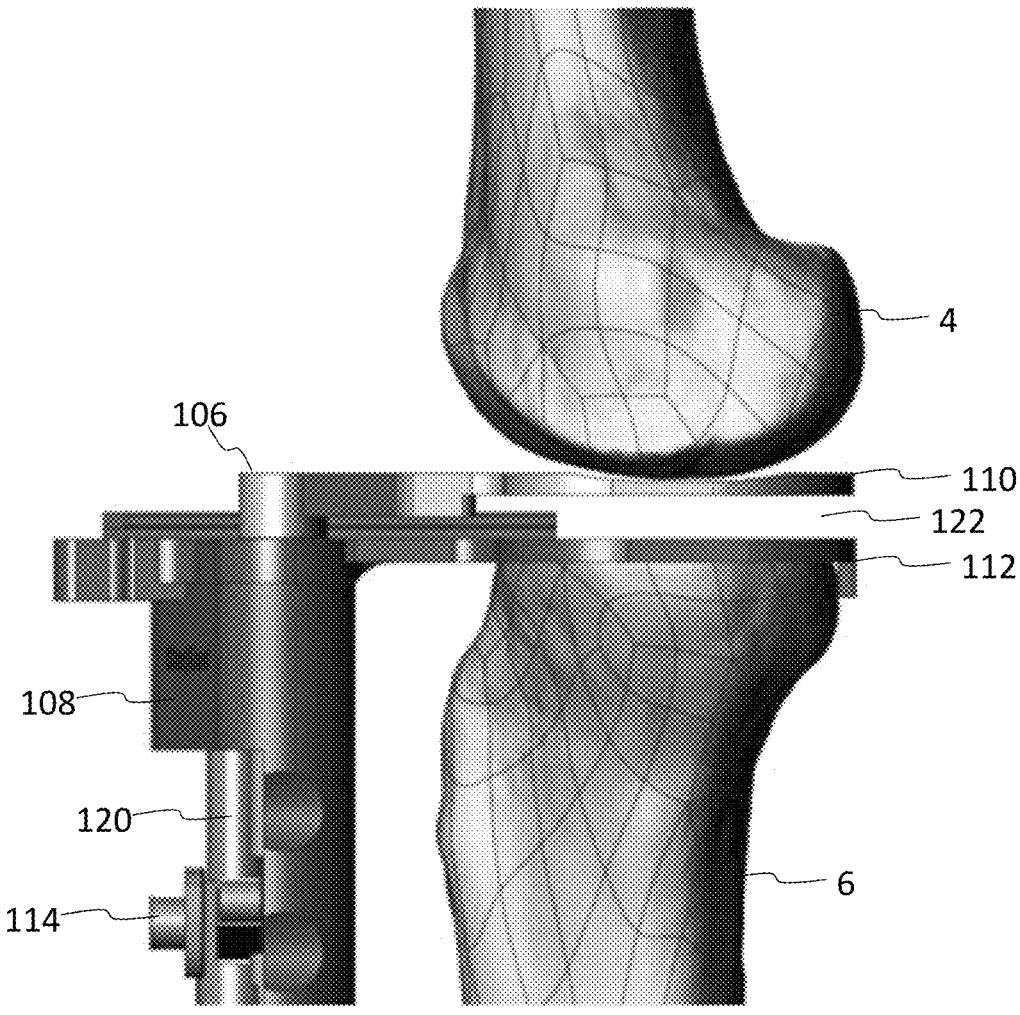
Figure 16:
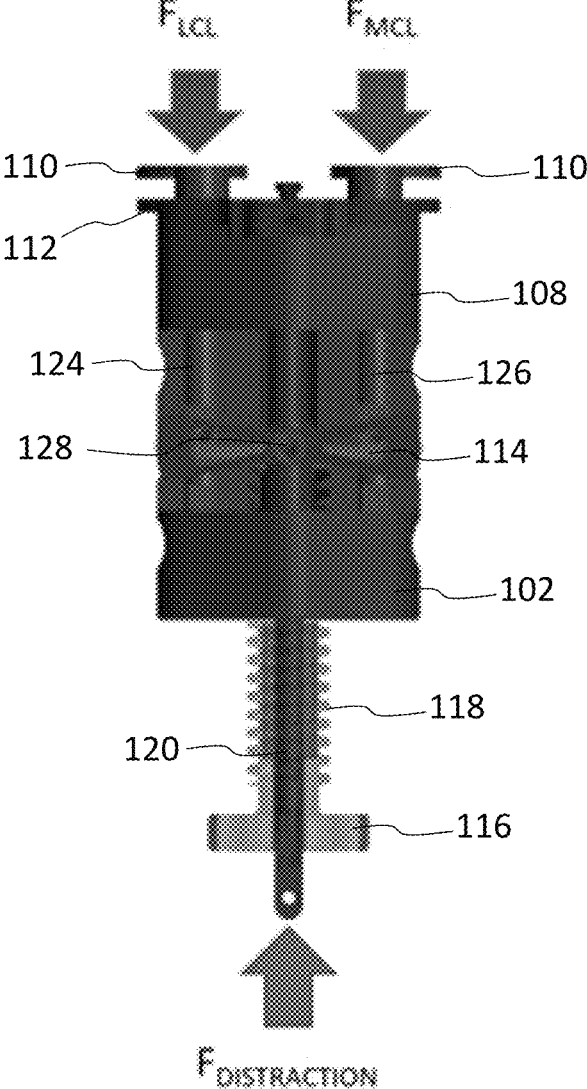
Figure 17:
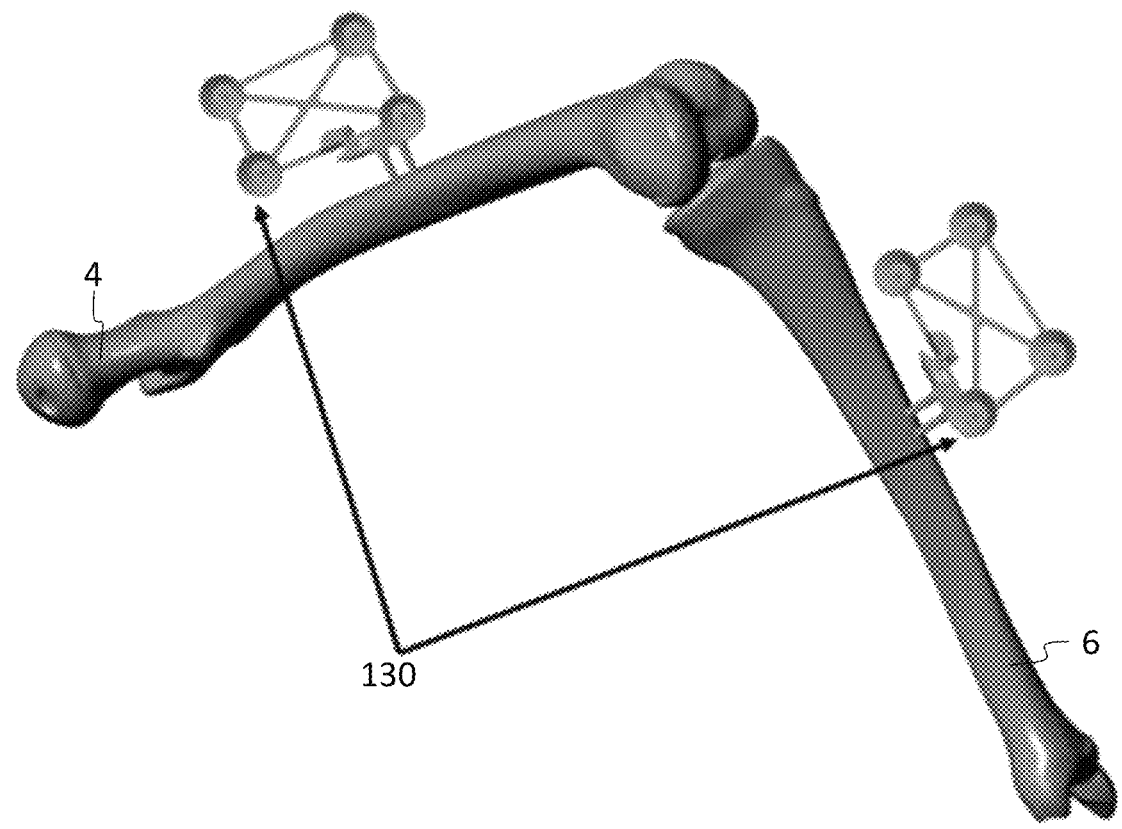
Figure 18A:
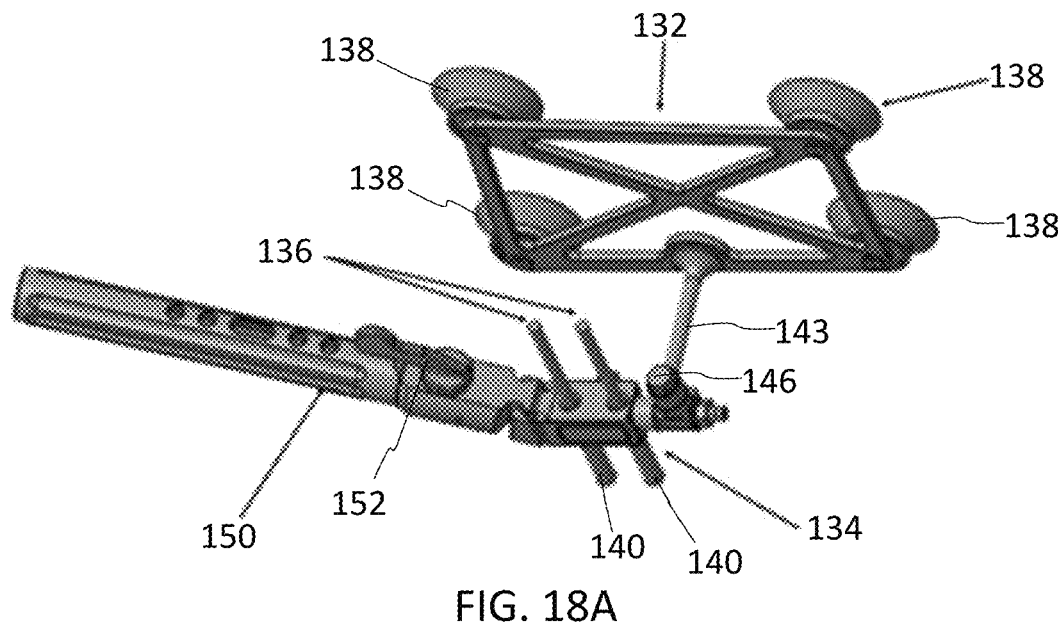
Figure 18B:
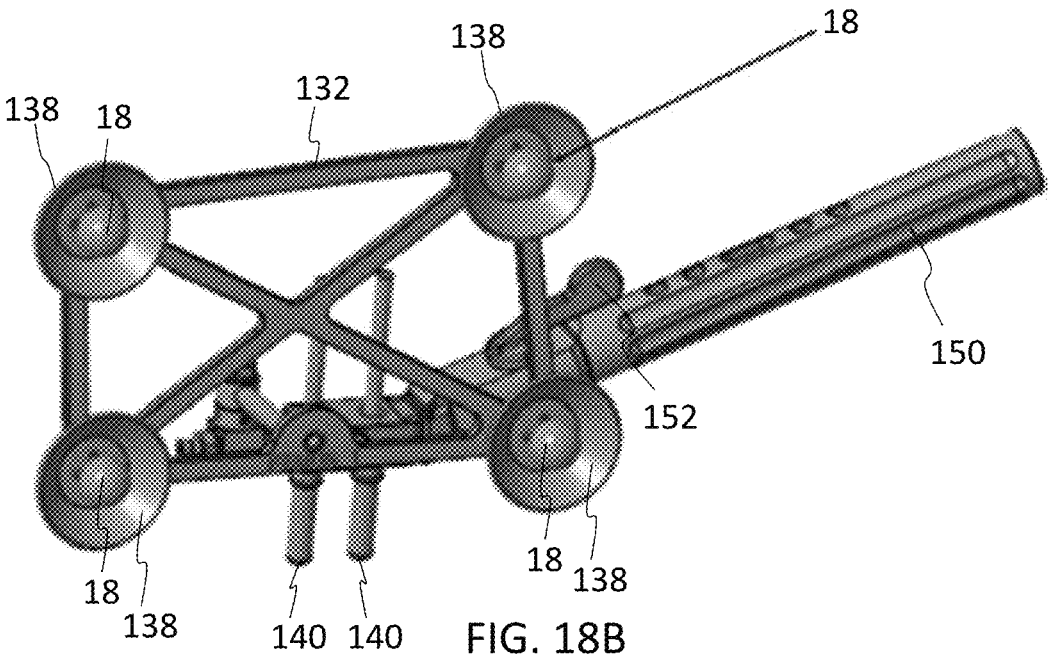
Figure 21:
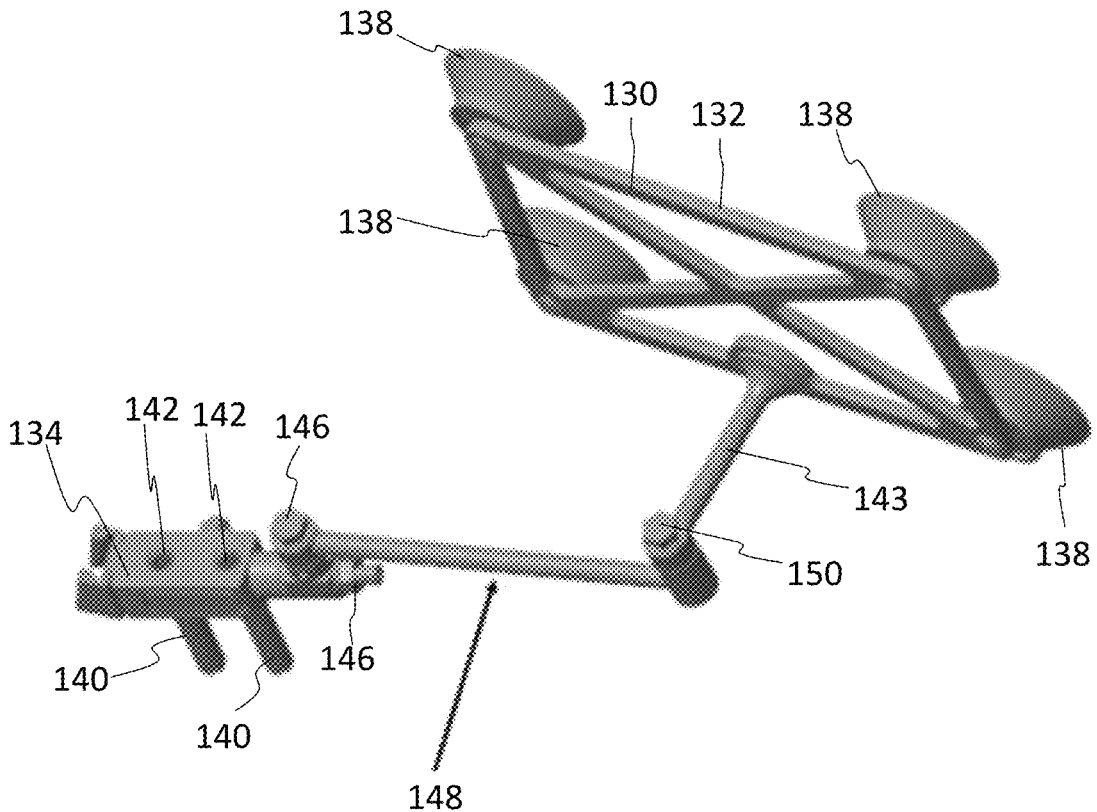
Figure 22A:
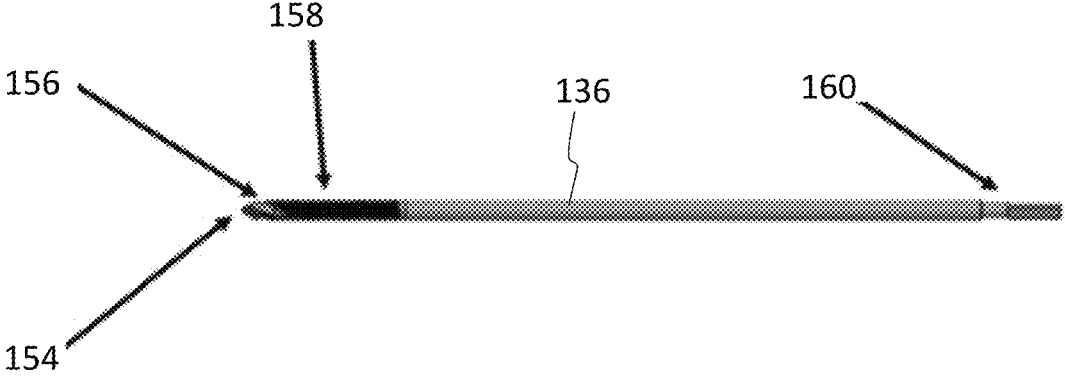
Figure 22B:
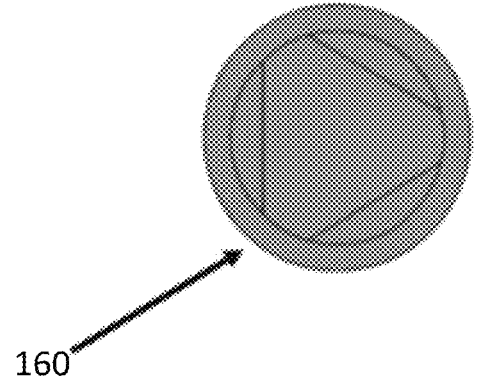

FIGS. 7A-7B illustrate embodiments of one or more surveillance markers that may be used to maintain navigation integrity;

FIG. 8 is an example of a landmark check using the surveillance marker and a stylus;

FIGS. 9A-9B illustrate embodiments of one or more virtual landmarks using a stylus;

FIG. 10 is an embodiment of a dynamic reference base with an integrated surveillance marker;

FIGS. 11A-11B show an embodiment of a plane checker;

FIGS. 12A-12B illustrate embodiments of the stylus that allow for landmark and/or point capture without the need for depressing the foot pedal of the robot during the operation;

FIG. 13 illustrates an embodiment of a tensor instrument for use during flexion of the femur and tibia;

FIG. 14 shows an embodiment of the tensor instrument;

FIG. 15 illustrates the tensor for use during extension of the femur and tibia;

FIG. 16 is an example of the tensor with ligament balance;

FIG. 17 is an illustration of a femur and tibia with a dynamic reference base attached to each bone;

FIGS. 18A-18B show an embodiment of a modular dynamic reference base with a removeable handle for installing the dynamic reference base;

FIGS. 19A-19C depict inserting an integrated bridge and pin guide of the dynamic reference base with the attached handle, driving pins through the bridge and pin guide, and locking the pins to the bridge with a locking element;

FIGS. 20A-20C depict the dynamic reference base with the handle removed, attaching the reference array, adjusting the position and/or orientation of the reference array, and locking the final position of the reference array;

FIG. 21 shows an embodiment of the dynamic reference base with an extension arm between the bridge and the reference array; and FIGS. 22A-22B show an embodiment of the bone pin which may be used to fixate the dynamic reference base to the bone.

DETAILED DESCRIPTION OF THE INVENTION

During a knee replacement, knee arthroplasty, or total knee arthroplasty (TKA), one or more implants may be used to cap the ends of the femur and/or tibia that form the knee joint. The knee includes the femur or thighbone of the upper leg, the tibia or shin bone of the lower leg, and the patella or knee cap. A TKA may be desirable when osteoarthritis cause breakdown of joint cartilage and/or one or more bones in the knee, rheumatoid arthritis causes inflammation of the synovial membrane, or trauma causes damage to the bone and/or cartilage of the knee. Although a TKA is exemplified herein, it will be appreciated that other orthopedic or other surgical procedures may utilize the devices and systems described herein. In order to improve surgical outcomes, a surgical navigation and/or robotic system may be used to navigate one or more instruments and/or assist the surgeon with one or more surgical procedures.

Figure 1:
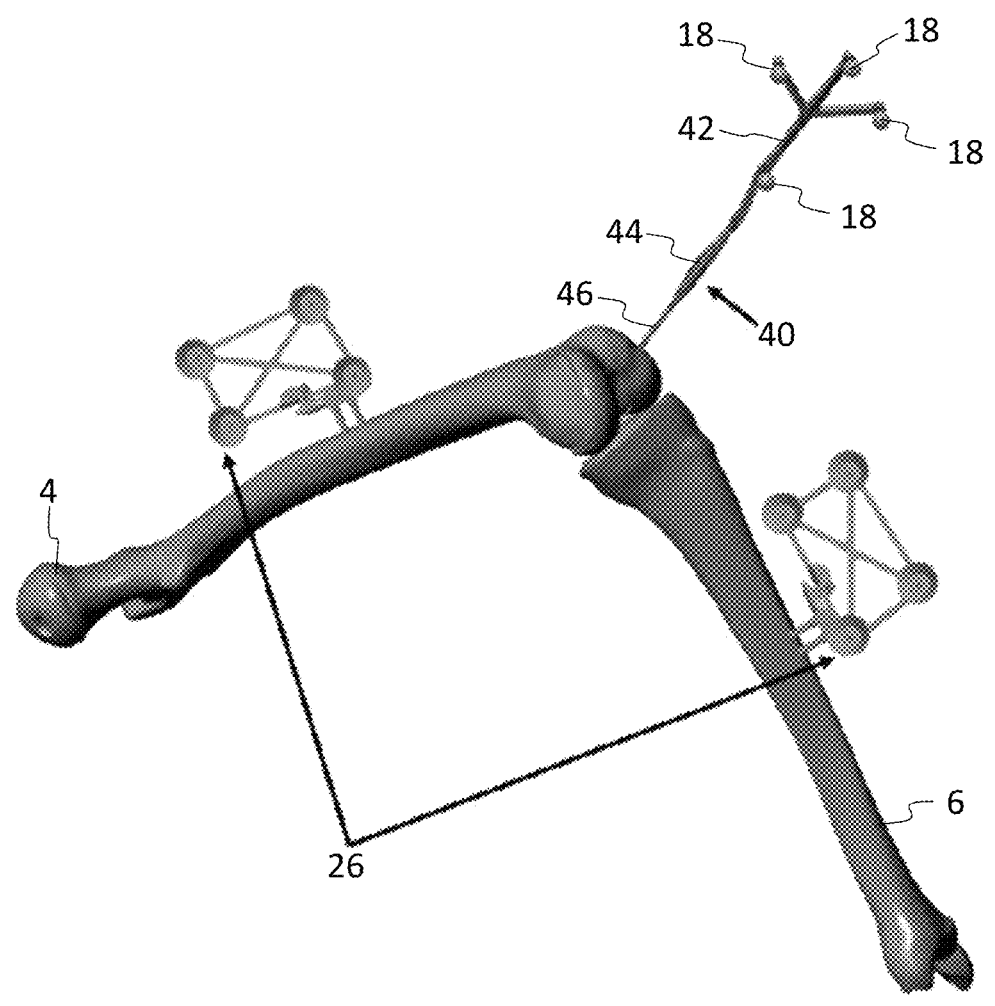
FIG. 1 shows a femur and tibia with a dynamic reference base attached to each bone and a stylus with a universal reference element according to one embodiment.
Figure 2:
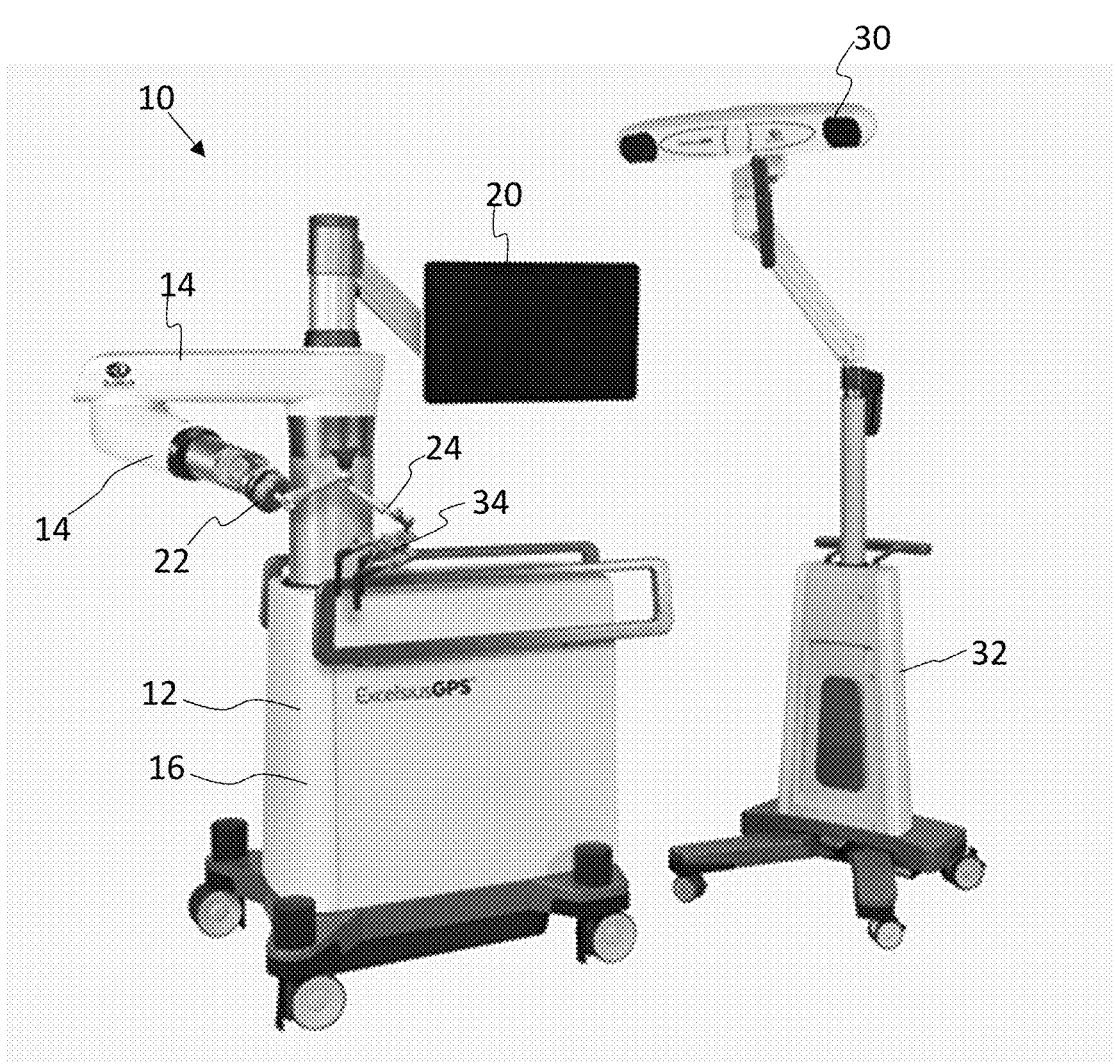
FIG. 2 illustrates a surgical robotic and/or navigation system in accordance with one embodiment.

Referring now to FIG. 1, a system or procedure for conducting one or more steps in a knee arthroplasty is shown. The femur 4 and tibia 6 are shown with a patient tracking device or dynamic reference base 26 attached to each bone. The dynamic reference base 26 tracks the patient's anatomy throughout the course of the operation. The dynamic reference base 26 may be configured to be tracked by a surgical robot and/or navigation system 10, for example, as shown in FIG. 2. The surgical robot and/or

Figure 3:
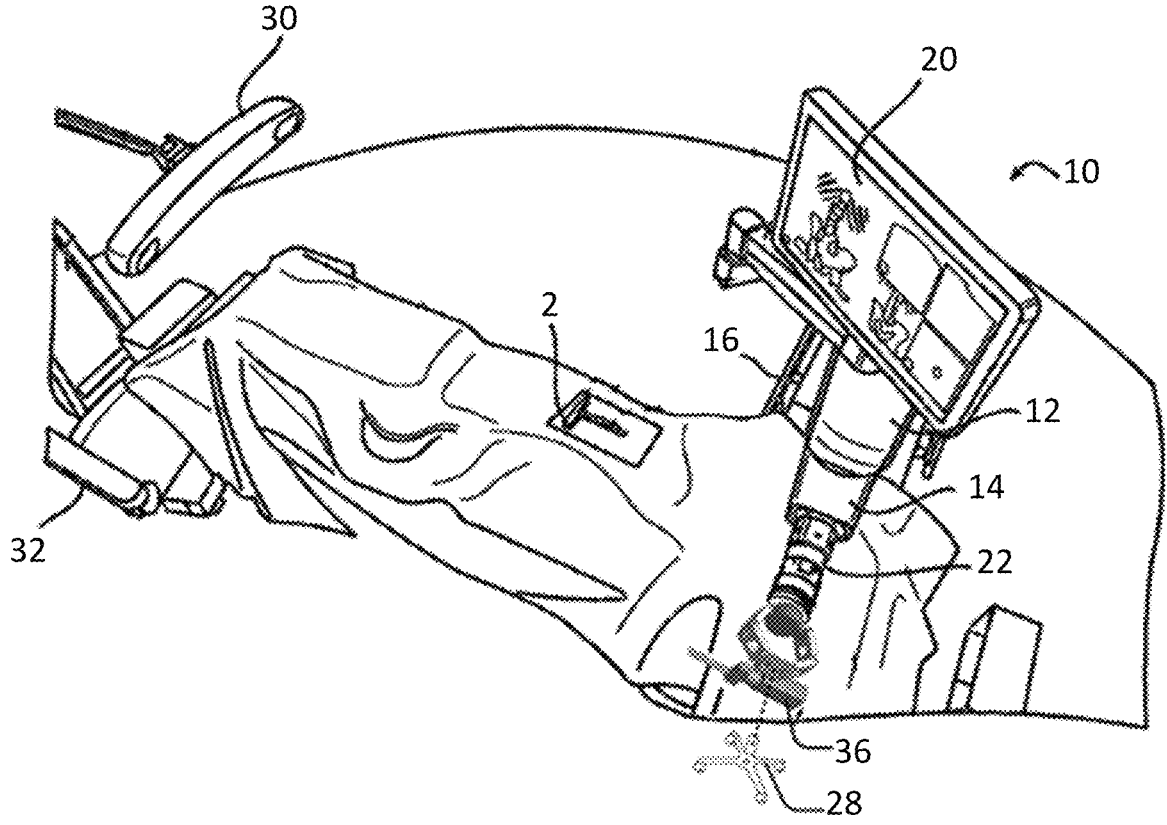
FIG. 3 illustrates a medical operation in which the sur-gical robot and camera system are positioned around a patient.

6 navigation system 10 may include, for example, a surgical robot 12, one or more robot arms 14, a base 16 including a computer platform, a display or monitor 20 (and/or optional wireless tablet, headset, etc.), an end-effector 22, and one or more tracking markers 18. The end effector 22 may be configured to secure a guide tube, access instrument, or other tool suitable for performing one or more steps in the orthopedic procedure. In one embodiment shown in FIG. 2, an access instrument 34 (e.g., a retractor) is attached to the end-effector 22 with an articulating arm 24, and in an alternative embodiment shown in FIG. 3, an instrument holder for securing a surgical saw 36, for example, configured to oscillate a saw blade for cutting bone, is coupled to the end-effector 22. It will be appreciated that a suitable instrument or device may be connected to the end-effector 22 for control by robot 12.

In navigated and/or robot-assisted surgical procedures, one or more instruments may be tracked using a reference element, array, or dynamic reference array 28, 42, 94. The reference array 28, 42, 94 may include one or tracking markers 18, which are attached or attachable to the instrument and allow for the tracking system 10 to detect and localize the position of the instrument in 3D space. The computer platform in combination with the camera tracking system or other 3D localization system are configured to track in real-time the pose (e.g., positions and rotational orientations) of the reference arrays 28, 42, 94. The tracking of 3D coordinates of the reference array 28, 42, 94 may allow the surgical system 10 to determine the pose of the reference array 28, 42, 94 in any multidimensional space in relation to the target anatomical structure of the patient 2.

The surgical robot system 10 may include one or more patient tracking devices or dynamic reference bases 26, 130 including one or more tracking markers 18, which are adapted to be secured directly to the patient 2 (e.g., to the bone of the patient 2). In the embodiment shown in FIG. 1, a first patient tracking device or first dynamic reference base 26 is secured to the femur 4 and a second patient tracking device or second dynamic reference base 26 is secure to the tibia 6 of the patient 2. In this manner, the system 10 is able to track the femur 4 and tibia 6 throughout the surgical operation.

The surgical robot system 10 may also utilize a camera 30, for example, positioned on a camera stand 32. The camera stand 32 can have any suitable configuration to move, orient, and support the camera 30 in a desired position. The camera 30 may include any suitable camera or cameras, such as one or more infrared cameras (e.g., bifocal or stereophotogrammetric cameras), able to identify, for example, active and/or passive tracking markers 18 in a given measurement volume viewable from the perspective of the camera 30. The camera 30 may scan the given measurement volume and detect the light that comes from the markers 18 in order to identify and determine the position of the markers 18 in three-dimensions. For example, active markers 18 may include infrared-emitting markers that are activated by an electrical signal (e.g., infrared light emitting diodes (LEDs)), and passive markers 18 may include retro-reflective markers that reflect infrared light (e.g., they reflect incoming IR radiation into the direction of the incoming light), for example, emitted by illuminators on the camera 30 or other suitable device.

The surgical robot 12 is able to control the translation and orientation of the end-effector 22. The robot 10 may be able to move end-effector 22 along x-, y-, and z-axes, for example. The end-effector 22 can be configured for selective rotation about one or more of the x, y-, and z-axis, and a Z Frame axis (such that one or more of the Euler Angles (e.g., roll, pitch, and/or yaw) associated with end-effector 22 can be selectively controlled). In some exemplary embodiments, selective control of the translation and orientation of end-effector 22 can permit performance of medical procedures with significantly improved accuracy.

The robotic positioning system 12 includes one or more computer controlled robotic arms 14 to assist surgeons in planning the position of one or more instruments relative to pre-operative and/or intraoperative patient images. The system 10 may include 2D & 3D imaging software that allows for preoperative planning, navigation, and guidance through dynamic reference arrays, navigated instruments and camera for the placement of instruments, orthopedic devices, or other devices. Further details of surgical robotic and/or navigation systems can be found, for example, in U.S. Pat. No. 8,257,360, U.S. patent publication No. 2019/0021795, and U.S. patent publication No. 2017/0239007, which are all incorporated herein by reference in their entireties for all purposes.

Figure 4A:
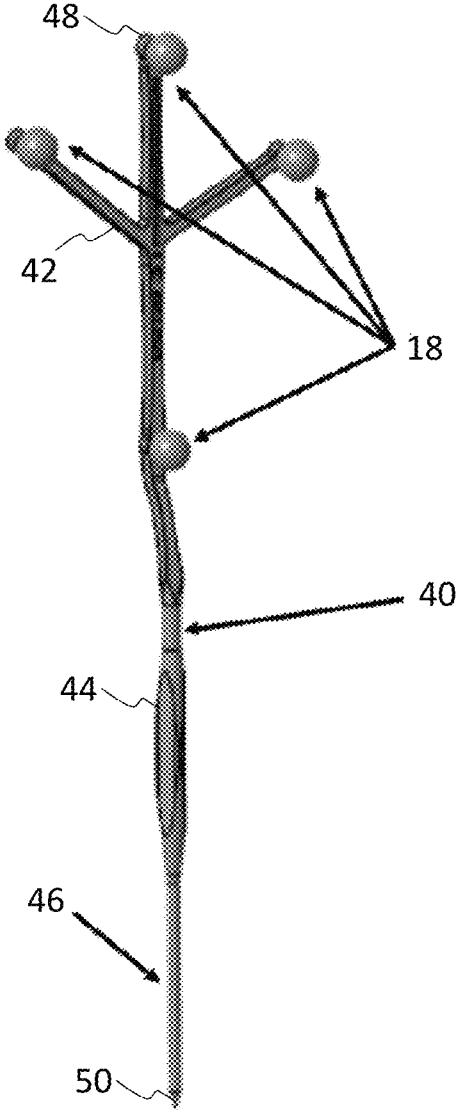
FIGS. 4A-4C illustrate embodiments of a stylus with a universal reference element, a plane checker instrument attached to the stylus, and a posterior tibial wall hook attached to the stylus.
Figure 4B:
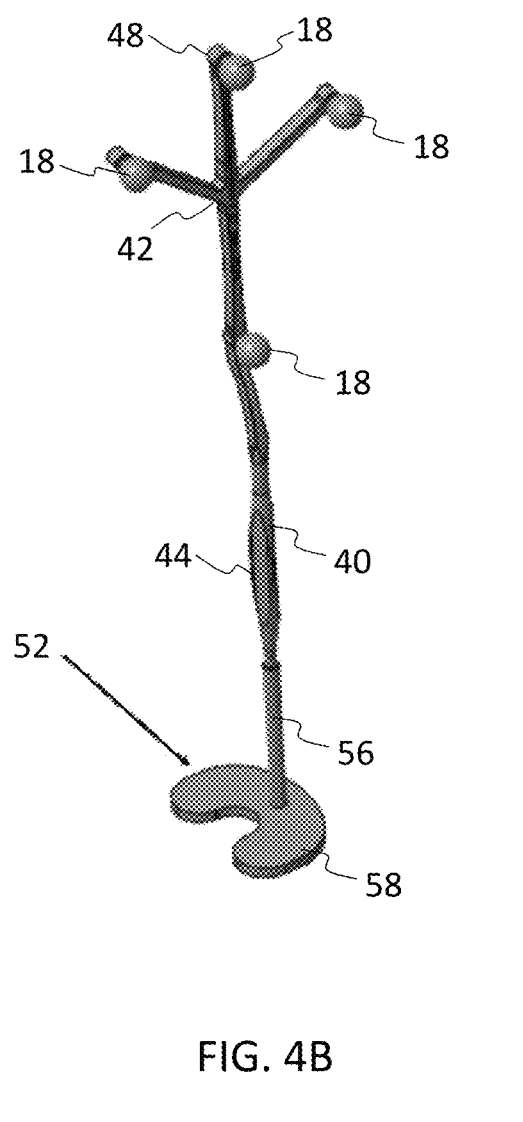
Figure 4C:
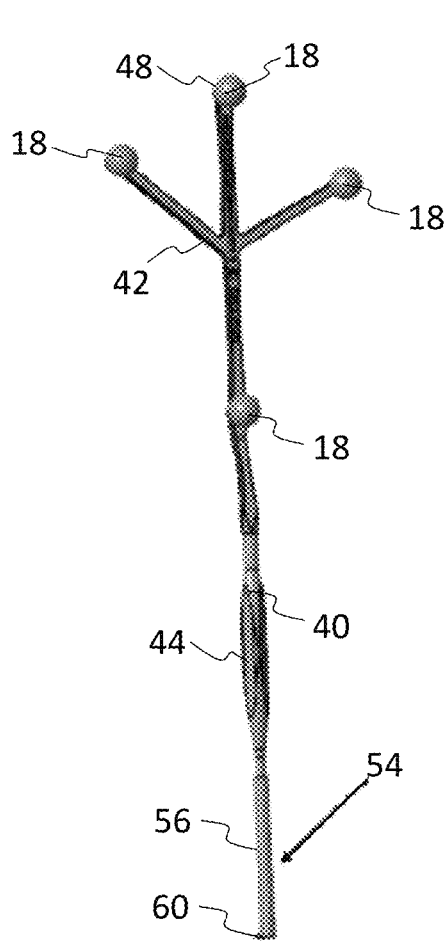

Turning now to FIGS. 4A-4C, embodiments of a universal stylus instrument or stylus 40 is shown. In navigated and/or robot-assisted surgical procedures, it may be common for several instruments to be tracked. If the user wishes to track different instruments, several different reference elements or arrays may be used with each having a different configuration. These unique configurations communicate to the navigation system 10 that a new instrument is being used and redefine its location in 3D space. Thus, in order to track many instruments, many corresponding reference elements are needed, which adds to the cost and complexity as the user is constantly reaching for and configuring different reference elements.

According to one embodiment, the stylus 40 is used as a universal reference element. The stylus 40 may be plugged into several different instruments to make each navigable, thereby eliminating the need for many different reference elements. As best seen in FIG. 4A, the stylus 40 may include an array 42 with a plurality of markers 18 at a proximal end 48, an elongate body 44, and a universal quick-connect attachment tip 46 at a distal end 50. The universal attachment tip 46 is configured to quickly attach the stylus 40 to one or more instruments and return their position to the navigation system 10. For example, in TKA, the stylus 40 may be used to navigate itself, an attached plane checker 52, an attached posterior tibial wall hook 54, or any other suitable instruments. The tracking markers 18 on the array 42 of the stylus 40 are viewable by the navigation system 10 and return the location of the stylus tip 46 and any attached instruments.

The universal stylus 40 may be used alone or with attached instruments (e.g., posterior tibial wall hook 54 or plane checker 52). A mechanical connection of the universal stylus 40 to the instruments 52, 54 may allow for the functional length between the navigated tip 46 of the instrument (e.g., measurement surfaces of the hook 54 or plane checker 52) and pattern of the stylus reference array 42 to be controlled with a high level of repeatability. The universal tip 46 may act as a quick connect mechanism for fast attachment of the instrument by the user.

In one embodiment shown in FIG. 4B, a plane checker 52 is attached to the stylus 40. The universal attachment tip 46 may be inserted into and secured to the plane checker 52. The plane checker 52 may include a collar 56 and a foot 58. The collar 56 may include a longitudinal opening configured to receive the universal tip 46 of the stylus 40. The universal attachment tip 46 of the stylus 40 may be sized such that it forms a clearance fit with the opening in the collar 56. If desired, a spring preloaded mechanism may be positioned in the opening such that it preloads the connected parts to a reference surface. The plane checker 52 may be free to rotate relative to the stylus 40. Free rotation of the plane checker 52 around the longitudinal axis A of the stylus 40 may allow the user to quickly reorient the reference array 42, for example, to ensure line of sight to the camera 30. Although a clearance fit is described, any suitable connection between the tip 46 and plane checker 52 may be used to temporarily secure the components together. The foot 58 may include a U-shaped plate or other suitably shaped plate. The foot 58 may include a flat bottom surface or flat portion configured to contact a resection surface on the bone. When used during a TKA procedure, the plane checker 52 may be used to ensure that the angulation and/or location of the resection plans matches the plane.

In another embodiment shown in FIG. 4C, a posterior tibial wall hook 54 is attached to the stylus 40. The universal attachment tip 46 may be inserted into and coupled to the posterior tibial wall hook 54. The universal attachment tip 46 of the stylus 40 may be sized such that it forms a location fit with the opening in the collar 56. A static fit may allow for a fixed position and orientation of the posterior tibial wall hook 54 with respect to the stylus array 42. Although a static fit is described, any suitable connection between the tip 46 and wall hook 54 may be used to temporarily secure the components together. The wall hook 54 may include collar 56 with an enlarged tip or hook 60 at its distal-most end. When used during a TKA procedure, the posterior tibial wall hook 54 may be used to localize the tibial wall.

Figure 5A:
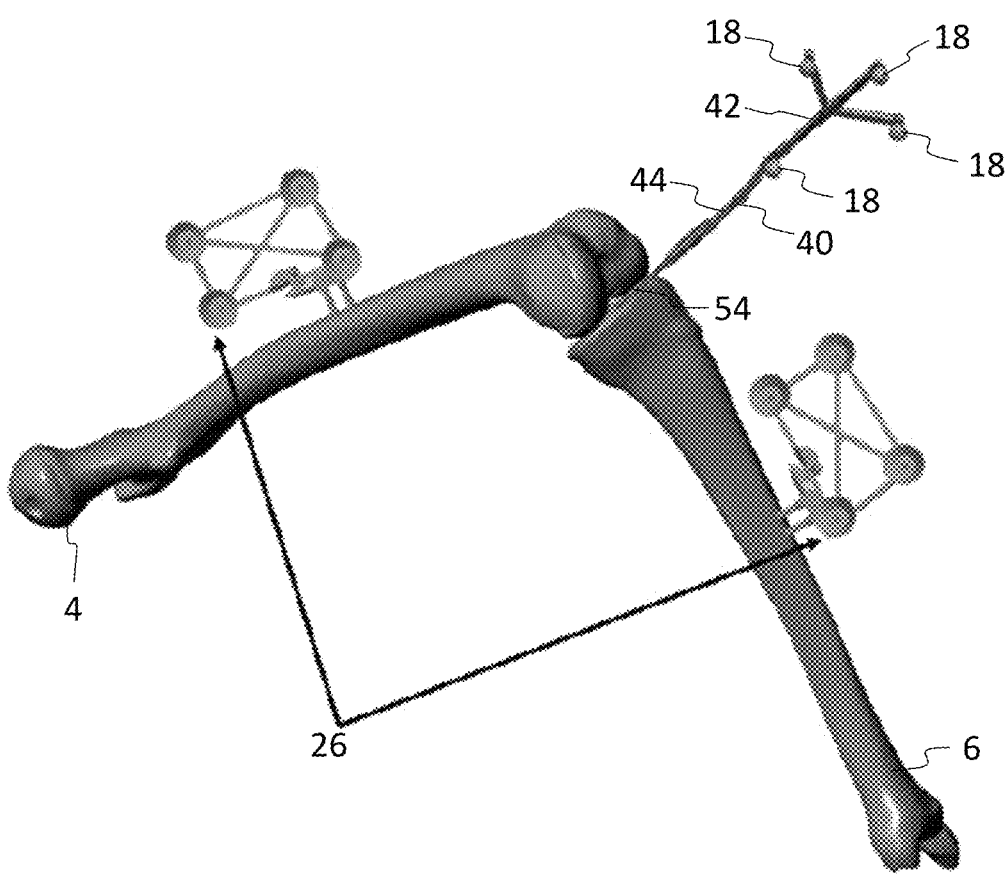
FIGS. 5A-5B show uses for the stylus with the tibia wall hook and plane checker attachment, respectively.
Figure 5B:
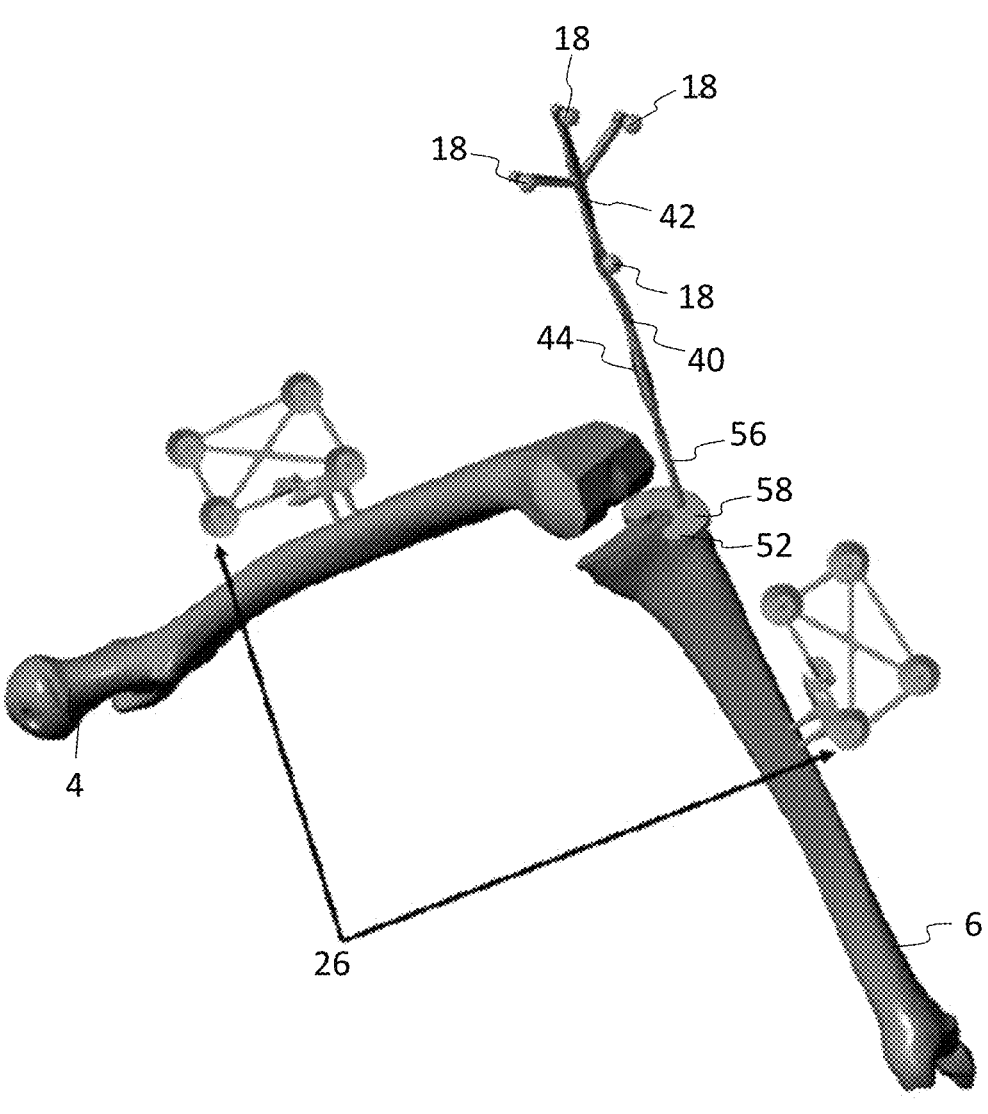

As shown in FIG. 1, the stylus 40 may be used alone. In this case, the dynamic reference bases 26 are tracking the patient anatomy of the femur 4 and tibia 6. The stylus 40 may be used for tasks such as landmark checks or characteristic bone surface acquisition including condyles or tibial plateau. In FIG. 5A, the tibial wall hook 54 has been attached to the distal end 50 of the stylus 40 via the attachment tip 46. When attached to the stylus 40, the hook 54 may be navigated via the stylus tracking array 42 and the user may perform acquisition of points to define the posterior tibial wall, for example. In FIG. 5B, the user may check the angulation and/or location of the resected planes using the attached plane checker 52. The plane checker 52 is attached to the universal tip 46 of the stylus 40, and the stylus 40 acts as a universal reference element for the plane checker 52. The resection planes determined by the plane checker 52 may be returned to the user via the navigation system 10.

Figure 6:
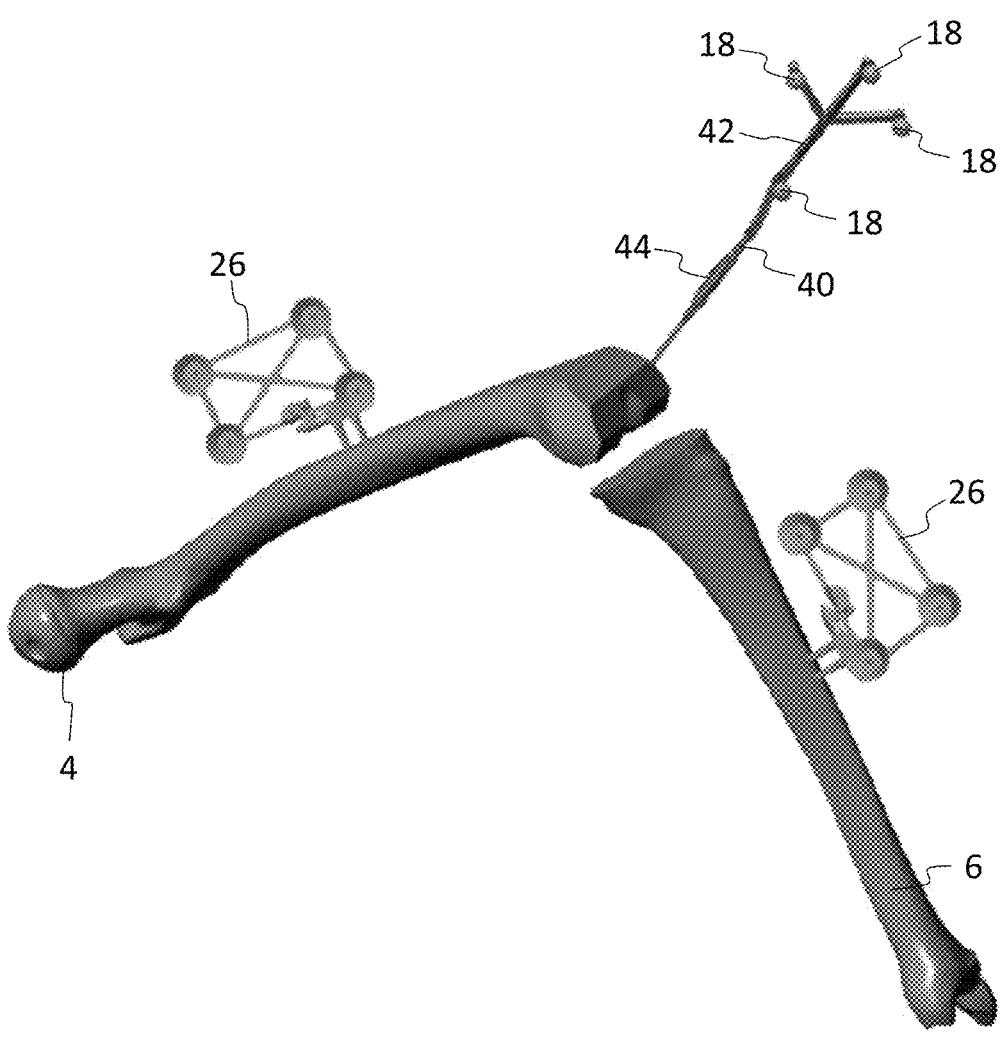
FIG. 6 shows a resected femur and resected tibia and a stylus according to one embodiment.

Turning now to FIG. 6, a resected femur 4 and tibia 6 are shown for a registered patient during a TKA procedure. As shown in FIG. 1, the patient has dynamic reference bases 26 inserted into the tibia 6 and femur 4 and after registration is complete, the stylus 40 may be used to perform landmark checks and establish confidence in the navigational integrity. As can be seen in FIG. 6, however, landmark checks are significantly more challenging post resection as most of the unique bony anatomy has been resected. In robotic and navigated TKA, it is important for the surgeon to have confidence that the patient's anatomy has been accurately registered to the system 10 and that the accuracy is maintained throughout the course of the operation. Navigational integrity may be used to describe this confidence. Specifically, in TKA, navigational integrity may be challenging to maintain throughout the course of the procedure due to the primary anatomical landmarks that the surgeon may use as reference points being resected during the operation.

Accordingly, one or more embodiments described herein provide for the user to perform physical landmark checks even after bony resection removes natural landmarks. One or more embodiments described herein provide for surveillance of the dynamic reference base 26 to ensure that any relative motion to the dynamic reference base 26 is identified and/or recorded. These techniques serve to increase the user's ability to establish and maintain confidence in the system navigational integrity.

With emphasis on FIGS. 7A-7B, according to one embodiment, one or more surveillance markers 62 may be used to maintain navigational integrity throughout the procedure. For example, a patient registration may include the addition of a first surveillance markers 62 in the femur 4 and a second surveillance marker 62 in the tibia 6 in areas that will not be resected during the procedure. As shown in FIG. 7B, the surveillance marker 62 may include a body 64 including a fastener 66 terminating at a distal tip 68, a verification divot 70, and a tracking marker 18. The fastener 66 may include a bone pin, screw, or anchor, which is inserted into the patient's bony anatomy. The distal tip 68 may be pointed, sharp, or otherwise configured to engage bone. The verification divot 70 may be integrated into the body 64 of the surveillance marker 62. A single tracking marker 18 may be attached to the top of the marker 62, for example, near the verification divot 70.

Once inserted into the patient, the location of the surveillance marker 62 may be registered relative to the dynamic reference base 26. The registration stores the virtual distance between the surveillance marker 62 and the dynamic reference base 26. If the dynamic reference base 26 moves (for example, if it was bumped by the user), the system 10 measures the distance and alerts the user when a movement threshold, for example, 2 mm is exceeded. If the user would like to verify or re-establish the navigational integrity, an additional landmark check may be conducted using the verification divot 66 in the surveillance marker 62 as shown in FIG. 8. For example, the tip 46 of the stylus 40 may be inserted into the verification divot 70 of the surveillance marker 62, thereby confirming navigational integrity.

In an alternative embodiment shown in FIGS. 9A-9B, the surveillance marker(s) may be replaced with one or more virtual landmarks 72 in order to maintain navigational integrity throughout the procedure. For example, a first virtual landmark 72 may be positioned in the femur 4 and a second virtual landmark 72 may be positioned in the tibia 6 in areas that will not be resected. The virtual landmark 72 may include a fastener 74, such as a cortical bone screw, with a verification divot 76, for example, nested in the drive feature of the screw. The fastener 74 may include a threaded shaft 78 and an enlarged head 80. As shown in FIG. 9A, the virtual landmarks 72 may be inserted into the patient's bony anatomy at the start of the procedure and the location returned to the system 10 using the stylus 40. If the user would like to perform an intraoperative landmark check at any time (including after resection), the user simply inserts the distal tip 46 of the stylus 40 into the divot 76 of the virtual landmark 72.

In an alternative embodiment shown in FIG. 10, a surveillance marker 82 may be integrated into the dynamic reference base 26 in order to maintain navigational integrity throughout the procedure. The surveillance marker 82 may be affixed the dynamic reference base 26 with a bridge 84 and one or more arms 86. The surveillance marker 82 may be affixed to the bridge 84, for example. The distance between the reference element of the dynamic reference base 26 and the surveillance marker 82 is stored by the system 10. If the dynamic reference base 26 and/or surveillance marker 82 is bumped and/or rotated about the axis indicated, the change in distance and/or movement would be identified and recorded by the system 10 and the user immediately alerted to the disruption.

In an alternative embodiment shown in FIGS. 11A-11B, a plane checker instrument 90 may be used to maintain navigational integrity even if traditional anatomical landmarks are removed during the procedure. The plane checker 90 may include a body 92 with a reference element or array 94 including a plurality of tracking markers 18, a shaft 96 extending from the body 92, and a foot 98 at the distal end of the shaft 96. The array 94 is located in a known location relative to the foot 98. The foot 98 may include a U-shaped plate or other suitably shaped plate with a flat bottom surface 100. When used during a TKA procedure, the plane checker 90 may be used to ensure that the angulation and/or location of the resection plans matches the plane. As shown in FIG. 11A, after resection of the femur 4 and/or tibia 6, the foot 98 includes a flat surface 100 which can be placed on the resection planes, and returns to the system 10 an angulation and cut depth. Using this information, the user is able to localize their position and maintain navigation integrity even after the traditional anatomical landmarks have been resected.

Turning now to FIGS. 12A-12B, embodiments of stylus 40 is shown. In navigated and robotic TKA, the surgeon may need to capture anatomical landmarks or points in order to register the patient anatomy to the system 10, establish and maintain confidence in the system's navigational integrity, and/or localize trials and implants to compare planned to placed accuracy. FIG. 1 shows one setup for navigated and/or robotic TKA. Dynamic reference bases 26 are attached to the femur 4 and tibia 6, and after being registered, the system 10 is able to track the location of each bone in 3D space. The navigated stylus 40 may be used for landmark localization and/or point acquisition. In one workflow, the stylus tip 46 is located at the point of interest and a foot pedal on the robot 12 is pressed to capture the point on the system 10. In this embodiment, the point capture depends on the surgeon pressing the foot pedal that is linked to the system 10.

The foot pedal method of point capture may be problematic if the foot pedal location on the operating room (OR) floor is unknown. For example, the foot pedal may be unintentionally kicked or moved out of reach of the surgeon. If this happens, the surgeon may need to change their focus from the operative field to search for the foot pedal. In addition, cables linking the foot pedal may be problematic, for example, as a trip hazard or obstructing free passage of equipment in the OR. Also, software may need to handle disabling other functionality, such as robot control, that may also be linked to the foot pedal before enabling point capture functionality, which adds complexity to the software algorithms. Accordingly, it may be desirable to include additional embodiments that could be used in place of the traditional foot pedal.

FIG. 12A shows an alternative setup for navigated and/or robotic TKA. FIG. 12A shows a similar setup to FIG. 1 except in this setup, once the point of interest has been localized by the stylus tip 46, the surgeon may rotate the stylus 40 about its long vertical axis by a threshold rotation. By rotating the stylus 40, the markers 18 move from a first position (prior to rotation) to a second position (after rotation). The stylus 40 may rotate about its axis by a threshold rotation of, for example, about 30°, about 60°, about 180°, or any suitable degree to indicate rotation. This rotation is captured by the system 10, and the point of interest is returned, thereby capturing the landmark by the system 10 without depressing the foot pedal or other button. To ensure that the system 10 behaves as intended while the surgeon is identifying points versus moving the tool freely, the system 10 may use algorithmic rules to filter out false positives. For example, the system may check that the threshold rotation (e.g., at least 30° of rotation) occurs while the tip 46 moves less than a given amount (e.g., less than 0.5 mm). For example, if greater than 0.5 mm movement occurs at the tip 46 during the 30° rotation, then disregard the point capture. If less than 0.5 mm movement occurs at the tip 46 during 30° rotation, then capture the point/landmark.

FIG. 12B shows another embodiment for navigated and/ or robotic TKA. FIG. 12B shows a similar setup to FIG. 12A except in this embodiment, one tracking marker 18 associ- ated with the array 42 is physically movable once the stylus 40 is on the point of interest or landmark. For example, one tracking marker 18 may be moved from a first tracking marker position 18*a* to a second tracking marker position 18*b*. The surgeon may manually move the marker 18 by pressing it with their thumb or finger while holding the stylus tip 46 steady in place. The system 10 detects the movement of one array marker 18*a*, 18*b* relative to the others and captures the point of interest.

In yet further embodiments, the process may include point capture via a voice input from the user; point capture via blocking or revealing a tracking marker, or blocking then revealing one or more markers with a specific timing (e.g., equivalent of "double clicking"); point capture via gesture with the other hand, the face, or the elbow, captured and interpreted by visible light tracking; point capture by sync- ing stylus positioning with a metronome, such that at each beat, a new point is captured, which may be valuable if an articulation of a bone is being systematically digitized; or any other suitable point capture methods or techniques.

Turning now to FIG. 13, a tensor instrument or tensor 102 is shown with the femur 4 and tibia 6 in flexion. A goal of total knee arthroplasty (TKA) may be to obtain tensionally symmetric and balanced flexion and extension gaps. One method of achieving this is to use a gap balancing technique in which the femoral cuts (posterior femur 4 in flexion, distal femur 4 in extension) are performed parallel to the resected proximal tibia 6 with each collateral ligament equally ten- sioned to obtain rectangular flexion and extension gaps. The implants may follow this parallel placement, thereby main- taining tension once implantation is complete.

In robotic and/or navigated TKA, the patient's anatomy is registered to the computational system 10. After registration, the relative location of the patient's tibia 6 and femur 4 may be tracked allowing for real time updates on the computa- tional system 10 of the patient's gap measurements. With the assistance of the tensor 102, the surgeon may view quanti- fied ligament balancing on the navigation display 20. The tensor 102 may facilitate gap balancing by: (1) applying a distraction force between the tibia 6 and femur 4; and/or (2) applying the distraction force such that differing tension in the medial collateral ligament (MCL) and lateral collateral ligament (LCL) is transparent to the user.

As shown in FIG. 13, dynamic reference bases 26 are rigidly attached to the patient's tibia 6 and femur 4. During registration, the patient's anatomy is registered to the system 10 and tracked via the dynamic reference bases 26. Once the patient is registered, the surgeon may make a first resection. Post resection, the tensor 102 may be used to assess the gap balance. In the embodiment shown in FIG. 13, the proximal tibia 6 is resected and the tensor 102 is placed against the resection while the bones are held in flexion. In FIG. 15, the proximal tibia 6 is resected and the tensor 102 is placed against the resection while the bones are held in extension. It will be appreciated that the resections may be made following a femur first or tibia first approach.

With reference to FIG. 14, the tensor 102 may extend from a proximal end 104 to a distal end 106. The tensor 102 include a body 108 with a pair of independent superior distraction paddles 110 and an inferior distraction paddle 112 at the distal end 106, a central shaft 120 extending along the length of the body 108 configured to move the superior distraction paddles 110 relative to the inferior distraction paddle 112, a knob 116 at the proximal end 104 configured to move the superior distraction paddles 110, and a distrac- tion balancing spring 118 positioned around the shaft 120 between the body 108 and the knob 116.

The tensor 102 is configured to provide a distraction force between the tibia 6 and femur 4. The tensor 102 may allow for any imbalance between MCL and LCL tensions to be displayed by a ligament balance indicator 114 positioned on the body 108 of the tensor 102. The first superior distraction paddle 110 may be connected to a first end of the ligament balance indicator 114 with a first rod 124, and the second superior distraction paddle 110 may be connected to the opposite end of the ligament balance indicator with a second rod 126. The indicator 114 may be pivotably connected to the body 108 with a pivot pin 128. The distraction force may be provided, for example, by rotation of the distraction knob 116. Rotation of the distraction knob 116 may translate the superior distraction paddles 110 outwardly and away from the inferior distraction paddle 112, thereby providing a gap 122 between the superior and inferior distraction paddles 110, 112. As the tensor 102 applies the distraction force, the bony anatomy will move. This movement may be registered by the navigation system 10 and may be displayed for interpretation by the surgeon. Specifically, the movement of the femur and tibia are continuously captured (e.g., as the tensor 102 is adjusted) by the camera 30 through the DRB 26 tracking markers on both tibia and femur bones and the gap information is automatically determined by the com- puter 16 based on the 3-dimensional positions of the track- ing markers on the DRBs 26, rather than manually viewed on the tensor by the surgeon. The changing gap information may be continuously displayed/updated in the display 20 for interpretation by the surgeon and may also be used by the computer 16 to automatically determine whether the planned cuts of the tibia and/or femur need to be adjusted. In some cases, the computer 16 may modify the planned cuts based on the automatically determined gap information and dis- play the modified cut planes on the display 20 (preferably in a 3-D graphical representation relative to the bones similar to FIG. 15, which the surgeon can then grab with, for example, fingers or mouse and rotate the displayed bones, their spacing and desired cut planes in different directions or angle using all 6 degrees of freedom or at least pitch, yaw and roll) for inspection, approval or modification by the surgeon. The gap data may include the angles and spatial separation between the femur and tibia. The angles and spatial separation data may be 3-dimensional data. More- over, the graphical user interface of the computer 16 is configured to graphically display on the display 20 both the original cut planes and suggested modified cut planes, preferably in different colors such as red and blue, that are superimposed on top of each other for easy comparison by the surgeon.

With reference to FIG. 16, the distraction paddles 110, 112 of the tensor 102 endure forces when the tensor 102 is inserted and distracted between the femur 4 and tibia 6. For example, a distraction force $F_{DISTRACTION}$ presses against the inferior distraction paddle 112, a force $F_{LCL}$ is applied to the first superior distraction paddle 110, and a force $F_{MCL}$ is applied to the second superior distraction paddle 110. If the ligaments are in balance ($F_{LCL}=F_{MCL}$), as shown in FIG. 16, the ligament balance indicator 114 may indicate the balance. For example, the ligament balance indicator 114 may be shown generally horizontal. If the ligaments are not in balance ($F_{LCL}<F_{MCL}$, $F_{LCL}>F_{MCL}$), then the ligament balance indicator 114 may indicate the imbalance. For example, the ligament balance indicator 114 may be shown generally inclined. The lower side of the indicator 114 may indicate a greater amount of force on the respective superior distraction paddle 110. The indicator 114 may indicate the amount or degree of imbalance for each respective force.

According to one embodiment, a work flow for using the tensor 102 may include one or more of the following: (1) insert dynamic reference bases 26 in bone and register patient; (2) make a first resection (proximal tibia 6 or distal femur 4); (3) check ligament balance with tensor 102 in extension; (4) adjust implant plan accordingly; (5) make remaining resections; (6) check balance in flexion and extension; (7) adjust cuts if required; (8) insert femur trial and check balance in flexion and extension; (9) adjust tibia plan if required; and (10) complete procedure per standard practice. In this manner, the tensor 102 may facilitate gap balancing. By applying a distraction force between the tibia 6 and femur 4, the information may be displayed on the navigation screen 20 for interpretation by the user. In addition, the distraction force may be applied such that differing tension in the MCL and LCL is apparent to the user on the tensor 102.

Turning now to FIG. 17, an embodiment of a modular dynamic reference base 130 is described in further detail. In robotic and/or navigated TKA the patient's anatomy is registered to the system 10. The registration is facilitated by attaching one or more dynamic reference bases 130 to the bone. For example, a first dynamic reference base 130 may be rigidly attached to the femur 4 and a second dynamic reference base 130 may be rigidly attached to the tibia 6. Once registration is complete, the dynamic reference base(s) 130 enable tracking of the patient anatomy in real time.

Turning now to FIGS. 18A-18B, the dynamic reference base 130 may be modular, which may reduce the number of instruments used throughout the procedure. The modular dynamic reference base 130 may include a reference element or array 132 including a plurality of tracking markers 18, a bridge 134, and one or more fasteners or bone pins 136 for securing the dynamic reference base 130 to bone. The array 132 may include a rectangular frame with a cross brace. It will be appreciated, however, that the array 132 may include a suitable framework for supporting the tracking markers 18 in a desired configuration. In the embodiment shown, a tracking marker 18 is placed at each corner of the rectangular frame.

The tracking markers 18 may be protected from contamination via one or more physical barriers, protectors, or shields 138 configured to prevent loss of navigation intraoperatively. For example, each of the four tracking markers 18 may be positioned within a respective shield 138. The shields 138 may provide for protection for each of the individual tracking markers 18. The shield 138 may include a round shallow plate with a sloped side. It will be appreciated that the shield 138 may have any suitable configuration for protecting the tracking markers 18. In particular, the tracking markers 18 may be protected from contamination via the shields 138.

The dynamic reference base 130 may include an integrated bridge 134 and pin guide 140. The bridge 134 may include one or more through openings 142 and one or more pin guides 140 configured to receive bone pins 136. The pin guides 140 may include elongate channels configured to guide the bone pins 136 into bone. In the embodiment shown, the bridge 134 may include a first opening 142 aligned and in fluid communication with a first pin guide 140 and a second opening 142 aligned with and in fluid communication with a second pin guide 140. For example, the openings 142 and pin guides 140 may be generally aligned in parallel. It will be appreciated that any suitable number, location, and orientation of openings 142 and pin guides 140 may be selected to effectively attach the bridge 134 to bone. The dynamic reference base 130 may be attached to the patient via the bone pins 136. The bone pins 136 may include self-drilling bone pins. The bridge 134 may be locked to the pins 136 with a first locking screw 144. The integrated bridge 134 and pin guides 140 may reduce the number of instruments required and simplifying the work-flow of the procedure.

The dynamic reference base 130 may be attached to the patient with the bone pins 136 and bridge 134. Subsequently, the array 132 may be attached to the bridge 134, for example, with one or more legs 143. The dynamic reference base 130 may include a plurality of legs 143 offered in different lengths for intra and extra incision, which may increase workflow flexibility by facilitating extra and intra incision placement of the construct. The leg 143 may be affixed to the frame of the array 132 and attached to a distal end of the bridge 134. For example, as shown in FIG. 20A, the leg 143 may be positioned through an opening 141 in the bridge 134. As best seen in FIG. 20B, the leg 143 and attached array 132 may be configured to rotate about one or more axes. For example, the leg 143 and attached array 132 may be able to rotate about a longitudinal axis A1 of the bridge 134 and/or an axis A2 perpendicular to the bridge 134. Thus, the bridge 134 may facilitate adjustment about two axes A1, A2. As shown in FIG. 20C, after adjustment along the one or more axes, the array 132 may be locked into position with one or more locking screws 146.

As shown in FIG. 21, an optional extension arm or extension 148 may be provided to increase positioning options for the reference element 132. For example, a first end of the extension 148 may connect to the leg 143 at an additional pivot point 150 and a second end of the extension 148 may connect to the bridge 134. The locking screw 146 may secure the extension 148 in position. The extension 148 may increase positioning options for the reference element 132, thereby increasing workflow flexibility.

In order to install the modular dynamic reference base 130, a handle 150 may be attached to the bridge 134. The handle 150 may temporarily connect, for example, to the proximal end of the bridge 134. The handle 150 may include a thumb lock 152, for example, to ensure rigid fixation between the handle 150 and the bridge 134 during use. After the bridge 134 and bone pins 136 are installed, the handle 150 may be removed from the assembly.

A work flow for installing the modular dynamic reference base 130 may include one or more of the following: (1) make skin incisions on patient; (2) attach the handle 150 to the bridge 134 (shown in FIG. 19A); (3) insert the bridge 134 until it contacts cortical bone; (4) drive the bone pins 136 through the bridge 134 (shown in FIG. 19B); (5) lock the bridge 134 to the pins 136 using the locking screw 144 (shown in FIG. 19C); (6) remove the handle 150; (7) attach the reference element 132 to the bridge 134 (shown in FIG. 20A); (8) adjust the orientation of the reference element 132 (shown in FIG. 20B); (9) lock the adjustment via the locking screw 146 (shown in FIG. 20C); and (10) optionally, attach the extension 148 between the reference element 132 and the bridge 134 to facilitate more positioning options for the reference element 132 (shown in FIG. 21).

Turning now to FIGS. 22A-22B, an embodiment of a bone pin 136 is shown. The bone pin 136 may be used to fixate the dynamic reference base 130 to bone. The bone pin 136 may include a self-drilling tip 154, chip extraction flutes 156, and bone threads 158. The bone threads 158 may extend along a portion of the pin 136 and may have any suitable attributes including handedness, thread angle, lead, pitch, etc. The pins 136 may include a pin driver interface 160. The pin driver interface 160 may include an engagement surface configured to interface with a driver instrument to thereby install the pin 136. For example, the driver interface 160 may be configured to transfer axial insertion force and torque to the pin 136 to facilitate the pin 136 being driven into the patient anatomy.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A system for computer-assisted navigation during surgery, the system comprising:

a navigation system including a computer, a display coupled to the computer, and a camera coupled to the computer and configured to detect tracking markers;

a first dynamic reference base (DRB) including a first reference array with a plurality of tracking markers detectable by the camera, the first DRB configured to attach to and track a femur;

a second DRB including a second reference array with a plurality of tracking markers detectable by the camera, the second DRB configured to attach to and track a tibia; and a tensor including:

a body defining a central longitudinal axis;

first and second superior distraction paddles;

a paddle adjuster configured to move the first and second superior distraction paddles relative to the body;

an inferior distraction paddle;

a shaft connected to the paddle adjuster and positioned along the central longitudinal axis, the paddle adjuster configured to move the first and second superior distraction paddles relative to the inferior distraction paddle; and a spring positioned around the shaft between the body and the paddle adjuster;

wherein as the paddle adjuster is adjusted, the computer automatically determines gap information based on the 3-dimensional positions of the tracking markers of the first and second DRBs which are tracked by the camera, and displays on the display the determined gap information, and wherein the tensor includes a pivotable ligament balance indicator positioned on the body, wherein the first superior distraction paddle is connected to a first end of the ligament balance indicator with a first rod, and the second superior distraction paddle is connected to the opposite end of the ligament balance indicator with a second rod, the first rod and second rod are separate rods spaced apart from each other.

2. The system of claim 1, wherein the paddle adjuster includes a distraction knob and rotation of the distraction knob translates the superior distraction paddles outwardly and away from the inferior distraction paddle, thereby providing a gap between the superior and inferior distraction paddles.

3. The system of claim 1, wherein the spring includes one and only one spring that applies force to both the first and second superior distraction paddles.

4. The system of claim 1, wherein the tensor includes a pivotable ligament balance indicator positioned on the body, wherein the first superior distraction paddle is connected to a first end of the ligament balance indicator with a first rod, and the second superior distraction paddle is connected to the opposite end of the ligament balance indicator with a second rod.

5. The system of claim 4, wherein:

when the first and second superior paddles are distracted by the paddle adjuster, a distraction force $F_{DISTRACTION}$ is applied against the inferior distraction paddle, a force $F_{LCL}$ is applied against the first superior distraction paddle, and a force $F_{MCL}$ is applied against the second superior distraction paddle, and wherein if the ligaments are in balance where $F_{LCL}=F_{MCL}$, the ligament balance indicator indicates the balance, or if the ligaments are not in balance where $F_{LCL}<F_{MCL}$ Or $F_{LCL}>F_{MCL}$, then the ligament balance indicator indicates the imbalance.

6. The system of claim 1, wherein as the paddle adjuster is adjusted, the computer automatically and continuously determines the changing gap information based on the 3-dimensional positions of the tracking markers of the first and second DRBs which are tracked by the camera, and displays on the display the continuously determined changing gap information.

7. The system of claim 6, wherein the computer automatically determines whether any planned cut of the tibia or femur needs to be adjusted.

8. The system of claim 1, wherein the computer automatically:

determines whether any planned cut of the tibia or femur needs to be adjusted; and displays on the display a modified cut plane of the tibia or femur in a 3-D graphical representation.

9. A system for computer-assisted surgery, the system comprising:

a navigation system including a computer, a display coupled to the computer, and a camera coupled to the computer and configured to detect tracking markers;

a robot having a plurality of arms and an end effector adapted to be coupled to the arms, the end effector configured to hold a bone cutter for cutting along a plurality of cut planes that have been programmed by the computer;

a first dynamic reference base (DRB) including a first reference array with a plurality of tracking markers detectable by the camera, the first DRB configured to attach to and track a femur;

a second DRB including a second reference array with a plurality of tracking markers detectable by the camera, the second DRB configured to attach to and track a tibia; and a tensor including:

a body;

first and second superior distraction paddles;

a paddle adjuster configured to move the superior distraction paddles relative to the body;

an inferior distraction paddle;

a shaft connected to the paddle adjuster and positioned along the central longitudinal axis, the paddle adjuster configured to move the first and second superior distraction paddles relative to the inferior distraction paddle; and a spring positioned around the shaft between the body and the paddle adjuster;

wherein as the paddle adjuster is adjusted, the computer automatically determines gap information based on the 3-dimensional positions of the tracking markers of the first and second DRBs which are tracked by the camera, and displays on the display the determined gap information, and wherein the tensor includes a pivotable ligament balance indicator positioned on the body, wherein the first superior distraction paddle is connected to a first end of the ligament balance indicator with a first rod, and the second superior distraction paddle is connected to the opposite end of the ligament balance indicator with a second rod, the first rod and second rod are separate rods spaced apart from each other.

10. The system of claim 9, wherein the paddle adjuster includes a distraction knob and rotation of the distraction knob translates the superior distraction paddles outwardly and away from the inferior distraction paddle, thereby providing a gap between the superior and inferior distraction paddles.

11. The system of claim 9, wherein the spring includes one and only one spring that applies force to both the first and second superior distraction paddles.

12. The system of claim 9, wherein the tensor includes a pivotable ligament balance indicator positioned on the body, wherein the first superior distraction paddle is connected to a first end of the ligament balance indicator with a first rod, and the second superior distraction paddle is connected to the opposite end of the ligament balance indicator with a second rod.

13. The system of claim 12, wherein:

when the first and second superior paddles are distracted by the paddle adjuster, a distraction force $F_{DISTRACTION}$ is applied against the inferior distraction paddle, a force $F_{LCL}$ is applied against the first superior distraction paddle, and a force $F_{MCL}$ is applied against the second superior distraction paddle, and wherein if the ligaments are in balance where $F_{LCL}=F_{MCL}$, the ligament balance indicator indicates the balance, or if the ligaments are not in balance where $F_{LCL}<F_{MCL}$ Or $F_{LCL}>F_{MCL}$, then the ligament balance indicator indicates the imbalance.

14. The system of claim 9, wherein as the paddle adjuster is adjusted, the computer automatically and continuously determines the changing gap information based on the 3-dimensional positions of the tracking markers of the first and second DRBs which are tracked by the camera, and displays on the display the continuously determined changing gap information.

15. The system of claim 9, wherein the computer automatically determines whether any programmed cut plane of the tibia or femur needs to be adjusted.

16. The system of claim 9, wherein the computer automatically:

determines whether any planned cut of the tibia or femur needs to be adjusted; and displays on the display a modified cut plane of the tibia or femur in a 3-D graphical representation.

* * * * *